United States Patent
Yabunouchi et al.

[11] Patent Number: 5,854,165
[45] Date of Patent: Dec. 29, 1998

[54] TRANSITION METAL COMPOUND, CATALYST FOR OLEFIN POLYMERIZATION, PROCESS FOR PREPARING OLEFIN POLYMER BY USE OF CATALYST

[75] Inventors: Nobuhiro Yabunouchi; Kiyohiko Yokota; Masami Watanabe; Takuji Okamoto; Noriyuki Tani, all of Sodegaura, Japan

[73] Assignee: Idemitsu Kosan Co., Ltd., Tokyo, Japan

[21] Appl. No.: 619,513
[22] PCT Filed: Sep. 30, 1994
[86] PCT No.: PCT/JP94/01626
    § 371 Date: Mar. 29, 1996
    § 102(e) Date: Mar. 29, 1996
[87] PCT Pub. No.: WO95/09172
    PCT Pub. Date: Apr. 6, 1995

[30] Foreign Application Priority Data

| Sep. 30, 1993 | [JP] | Japan | 5-245129 |
| Dec. 22, 1993 | [JP] | Japan | 5-324208 |
| Jul. 8, 1994 | [JP] | Japan | 6-156948 |

[51] Int. Cl.⁶ ................................................. C08F 4/64
[52] U.S. Cl. .................. 502/117; 502/152; 502/155; 526/126; 526/127; 526/160; 526/170; 526/172; 526/943
[58] Field of Search ................... 502/117, 152, 502/155; 526/160, 943, 126, 127, 170, 172

[56] References Cited

U.S. PATENT DOCUMENTS 5,496,902  3/1996  Evertz et al. .................. 526/127

FOREIGN PATENT DOCUMENTS

93/20113  10/1993  WIPO.

OTHER PUBLICATIONS

Hawley et al., Hawley's Condensed Chemical Dictionary, 7th edition, p. 749, 1987.

Halterman, Ronald L. "Synthesis and Applications of Chiral Cyclopentadienyl Complexes", pp. 965–994, Mar. 1992.

Mengele et al. Organometallic, 1993, 12, pp. 1931–1935, "ansa–metallocene Derivatives. Chiral Zironocene Complexes with two Dimethylsilylene Bridges".

*Primary Examiner*—David W. Wu
*Attorney, Agent, or Firm*—Oblon, Spivak, McClelland, Maier & Neustadt, P.C.

[57] ABSTRACT

A transition metal compound which is a multiple crosslinking type transition metal complex represented by the general formula (I)

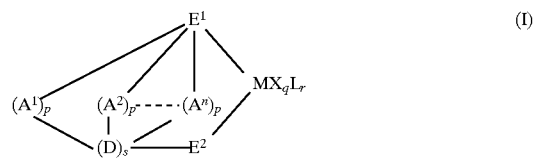

wherein M is a metallic element in the groups 3 to 10 or a lanthanoide series of the periodic table; $E^1$ and $E^2$ are each a σ-bonding or a π-bonding ligand; X is a σ-bonding ligand; L is a Lewis base; $A^1$, $A^2$ ... $A^n$ and D are each a crosslinking group; n is 2 to 4; p is 1 to 4; q is 1 to 5; r is 0 to 3; and s is 0 to 4; and catalysts for olefin polymerization containing the transition metal compound or complexes thereof and a process for preparing an olefin polymer employing the catalyst.

44 Claims, No Drawings

TRANSITION METAL COMPOUND, CATALYST FOR OLEFIN POLYMERIZATION, PROCESS FOR PREPARING OLEFIN POLYMER BY USE OF CATALYST

TECHNICAL FIELD

The present invention relates to a transition metal compound, a compound which can be used as its material, a process for preparing each of these compounds, a catalyst for olefin polymerization using the transition metal compound, an olefin polymer obtained by the use of this catalyst, and a process for preparing the olefin polymer. More specifically, the present invention relates to a novel multiple crosslinking type transition metal compound (multiple crosslinking metallocene complex) useful as a component of a catalyst for olefin polymerization, a bisindenyl derivative usable as a ligand of this transition metal compound, its precursor, a process for efficiently preparing each of the transition metal compound and its precursor, a catalyst for polymerization which has a high activity and an excellent copolymerizability and which contains the transition metal compound and which is capable of forming an olefin polymer having a uniform composition and a narrow molecular weight distribution, an olefin homopolymer and an olefin copolymer obtained by the use of this catalyst for polymerization, and a process for efficiently preparing each of these olefin polymers.

BACKGROUND ART

Heretofore, as highly active soluble catalysts for olefin polymerization, catalysts comprising a combination of a transition metal compound and an aluminoxane are known (Japanese Patent Application Laid-open Nos. 19309/1983 and 217209/1985). Furthermore, it has been reported that cationic species are useful as active species of the soluble catalyst for olefin polymerization [J. Am. Chem. Soc., Vol. 81, p. 81 (1959), Vol. 82, p. 1953 (1960), and Vol. 107, p. 7219 (1985)]. In addition, examples where each of these active species is isolated and is applied to the olefin polymerization have been described in J. Am. Chem. Soc., Vol. 108, p. 7410 (1986), Japanese PCT Patent Application Laid-open No. 502636/1989, Japanese Patent Application Laid-open No. 139504/1991 and EP-A-O 468651. Other examples where this active species is used together with an organic aluminum compound have been described in Japanese Patent Application Laid-open No. 207704/1991 and WO 92-1723. Moreover, an example of a catalyst for olefin polymerization which comprises a transition metal compound having a ligand containing an —$SO_3R$ group and an organic aluminum oxycompound has been described in EP-A-O No. 519746.

However, these catalysts do not always satisfy a catalytic activity for olefin polymerization, copolymerizability, and the uniformity and molecular weight distribution of an obtained polymer.

On the other hand, a transition metal compound having a bicyclopentadienyl group, i.e., a metallocene complex is particularly highly active and is known to be useful as a highly steric regular catalyst. This metallocene complex can be classified into a non-crosslinking type, a single crosslinking type and a multiple crosslinking type on the basis of the crosslinking structure of two cyclopentadienyl groups, but most of the conventional metallocene complexes are of the non-crosslinking type and the single crosslinking type.

Examples of the non-crosslinking type metallocene complex have been disclosed or reported in U.S. Pat. No. 5200537, Japanese Patent Application Laid-open Nos. 222177/1988, 222178/1988, 222179/1988, 301704/1989 and the like, and examples of the single crosslinking type metallocene complex have been disclosed or reported in Japanese Patent Application Laid-open Nos. 131488/1990 and 41303/1992, "Angew. Chem. Int. Ed. Engl.", Vol. 24, Vol. 6, p. 507 (1985) and the like.

On the contrary, with regard to the multiple crosslinking type (double crosslinking type) metallocene complexes, their synthetic examples are limited, and they are described only in WO 93-20113 and "Organometallics", Vol. 12, p. 1931 (1993). In addition, these publications have described a polymerization example of propylene in the presence of a dimethylsilylene double crosslinking type metallocene complex, but the heat stability of this catalyst itself is poor. Since this metallocene complex has a specific crosslinking structure, the isomerization of a meso form into a racemic form occurs during the preparation of the complex, and therefore the desired complex cannot always be obtained.

On the other hand, "Organometallics", Vol. 12, p. 5012 (1993) has described a preparation process of a bisindenyl derivative in which the crosslinking is made at the 2-position, but this process is not practical, because its synthetic route is intricate.

DISCLOSURE OF THE INVENTION

The present invention has been intended under such circumstances, and an object of the present invention is to provide (1) a novel multiple crosslinking type transition metal compound (multiple crosslinking metallocene complex) useful as a component of a catalyst for olefin polymerization, (2) a multiple crosslinking type bisindenyl derivative usable as a ligand of this transition metal compound, (3) a process for efficiently preparing the transition metal compound of the above-mentioned (1), (4) a bisindenyl derivative usable as a precursor of the multiple crosslinking type bisindenyl derivative of the above-mentioned (2), (5) a process for efficiently preparing the bisindenyl derivative of the above-mentioned (4), (6) a catalyst for polymerization which has a high activity and an excellent copolymerizability and which is capable of forming an olefin polymer having a uniform composition and a narrow molecular weight distribution, (7) an olefin homopolymer or copolymer having a uniform composition and a narrow molecular weight distribution obtained by the use of this catalyst for polymerization, and (8) a process for efficiently preparing the olefin homopolymer or copolymer.

Thus, the present inventors have intensively researched to achieve the above-mentioned object, and as a result, it has been found that a novel multiple cross-linking type transition metal compound having a specific structure is useful as a catalytic component for olefin polymerization; a specific multiple crosslinking type bisindenyl derivative is useful as a ligand of the above-mentioned transition metal compound; and the transition metal compound can efficiently be prepared by a specific process.

In addition, the present inventors have also found that a bisindenyl derivative, which can be used as a precursor of the multiple crosslinking type bisindenyl derivative useful as the ligand of the above-mentioned transition metal compound, can efficiently be prepared by a specific process.

Furthermore, the present inventors have found that a polymerization catalyst, which comprises the multiple crosslinking type transition metal compound, an activation cocatalyst, for example, a compound capable of reacting with the transition metal compound or its derivative to form an ionic complex, and if necessary, an organic aluminum compound, has a high activity and can efficiently provide an olefin homopolymer or copolymer having a uniform composition and a narrow molecular weight distribution.

In consequence, the present invention has been completed on the above-mentioned findings.

That is to say, according to the present invention, there can be provided (1) a transition metal compound represented by the general formula (I)

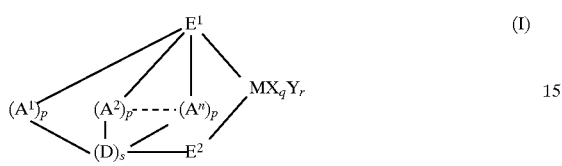

wherein M is a metallic element in the groups 3 to 10 or a lanthanoide series of the periodic table; $E^1$ and $E^2$ are each a σ-bonding or a π-bonding ligand, and they form a cross-linking structure via $(A^1)_p$, $(A^2)_p$, ... $(A^n)_p$ and $(D)_s$, and they may be the same or different; X is a σ-bonding ligand, and when a plurality of Xs are present, these plural Xs may be the same or different, and each X may crosslink with another X, $E^1$, $E^2$ or Y; Y is a Lewis base, and when a plurality of Ys are present, these plural Ys may be the same or different, and each Y may crosslink with another Y, $E^1$, $E^2$ or X; $A^1, A^2, \ldots A^n$ are each a crosslinking group, and they may be the same or different, but at least one of them comprises a crosslinked structure consisting of carbon alone; D is a crosslinking group, and when a plurality of Ds are present, these plural Ds may be the same or different; n is an integer of 2 to 4; p is an integer of 1 to 4, and the respective ps may be the same or different; q is an integer of 1 to 5 [(the valence of M)–2]; r is an integer of 0 to 3; and s is an integer of 0 to 4, and when s is 0, $(A^1)_p, (A^2)_p, \ldots (A^n)_p$, and $E^2$ form a direct bond, (2) a transition metal compound represented by the general formula (II)

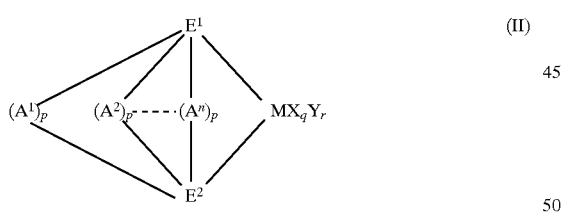

wherein M, $E^1, E^2, X, Y, A^1, A^2, \ldots A^n$, n, p, q and r are as defined above, (3) a multiple crosslinking type bisindenyl derivative represented by the general formula (III)

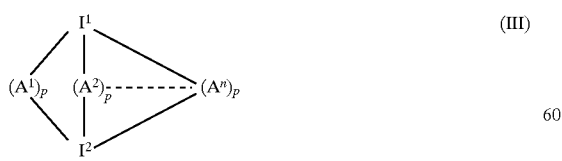

wherein $I^1$ and $I^2$ are each an indenyl group or a substituted indenyl group, and they form a crosslinking structure via $(A^1)_p, (A^2)_p, \ldots (A^n)_p$, and they may be the same or different; $A^1, A^2, \ldots A^n$ are each a crosslinking group, and they may be the same or different, but at least one of them comprises a crosslinked structure consisting of carbon alone; n is 2 or 3; and p is an integer of 1 to 4, and the respective ps may be the same or different, (4) a process for preparing a transition metal compound represented by the general formula (II)

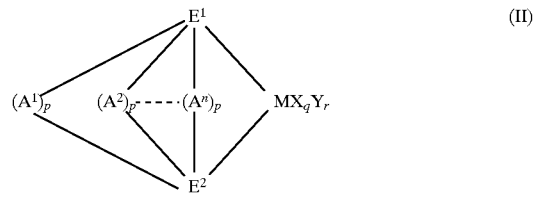

wherein M, $E^1, E^2, X, Y, A^1, A^2, \ldots A^n$, n, p, q and r are as defined above, said process comprising a step of dimetallizing a compound represented by the general formula (IV)

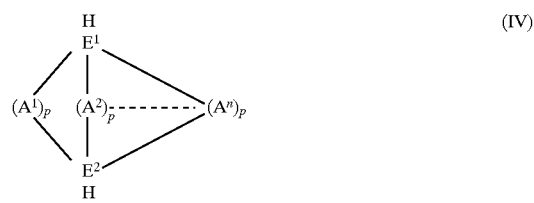

wherein $E^1, E^2, A^1, A^2, \ldots A^n$, n and p are as defined above, to obtain a compound represented by the general formula (V)

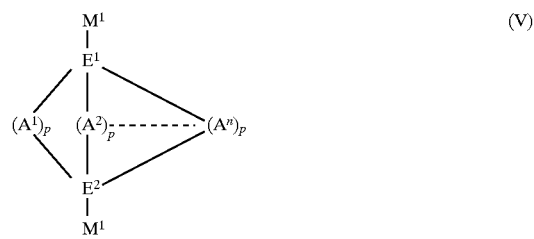

wherein $M^1$ is an alkali metal, an alkaline earth metal-containing salt residue or an organic aluminum residue, and $E^1, E^2, A^1, A^2, \ldots A^n$, n and p are as defined above, if necessary, a step of replacing $M^1$ with another metal containing an organic group or thallium, and a step of reacting, if necessary, in the presence of a Lewis base, the compound with a compound represented by the general formula (VI)

wherein M is a metallic element in the groups 3 to 10 or a lanthanoide series of the periodic table; X is a σ-bonding ligand; and q is an integer of 1 to 5 [(the valence of M)–2], and when a plurality of Xs are present, these plural Xs may be the same or different, and each X may crosslink with another X, (5) a bisindenyl derivative represented by the general formula (VII)

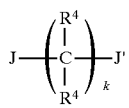 (VII)

wherein J and J' are each a group represented by the formula

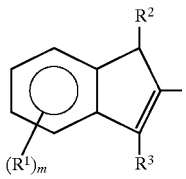

(wherein $R^1$, $R^2$ and $R^3$ are each a hydrogen atom, a hydrocarbon group having 1 to 20 carbon atoms, or a silicon-containing, an oxygen-containing or a halogen-containing group, and they may be the same or different, and when a plurality of $R^1$s are present, these plural $R^1$s may be the same or different and may bond to each other to form a ring structure, and $R^1$ and $R^2$ or $R^1$ and $R^3$ may bond to each other to form a ring structure; and m is an integer of 1 to 4), and J and J' may be the same or different; $R^4$ is a hydrogen atom, a hydrocarbon group having 1 to 20 carbon atoms, or a silicon-containing, an oxygen-containing or a halogen-containing group, and a plurality of $R^4$S may be the same or different, and they may be the same or different and may bond to each other to form a ring structure; and k is an integer of 1 to 20, but when k is 1 or 2, at least one of $R^4$s is not the hydrogen atom, (6) a process for preparing a bisindenyl derivative represented by the general formula (VII)
said process comprising
a step of reacting one or a mixture of two of compounds represented by the general formula (VIII)

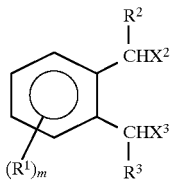 (VIII)

wherein $X^2$ and $X^3$ are each a halogen atom, and they may be the same or different; and $R^1$, $R^2$, $R^3$ and m are as defined above,
with an alkali metal or an alkaline earth metal in the presence of an organic solvent,
a step of reacting the reaction product with a compound represented by the general formula (IX)

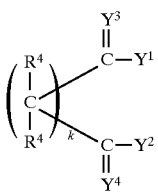 (IX)

wherein $y^1$ and $y^2$ is each $OR^5$, $NR^6{}_2$, $SR^7$ (wherein $R^5$ to $R^7$ are each a hydrogen atom, a hydrocarbon group having 1 to 20 carbon atoms, or a silicon-containing, an oxygen-containing or a halogen-containing group) or a halogen atom, and they may be the same or different; $y^3$ and $y^4$ are each O, S or $NR^8$ (wherein $R^8$ is a hydrogen atom, a hydrocarbon group having 1 to 20 carbon atoms, or a silicon-containing, an oxygen-containing or a halogen-containing group), and they may be the same or different; and $R^4$ and k are as defined above,
to obtain a compound represented by the general formula (X)

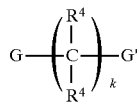 (X)

wherein G and G' are each a group represented by the general formula

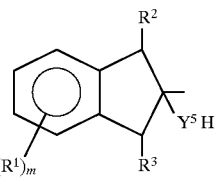

(wherein $Y^5$ is $Y^3$ or $Y^4$ (where $Y^5$ is $Y^3$ or $Y^4$), and G and G' may be the same or different; and $R^4$ and k are as defined above, and
a step of dehydrating the obtained compound, (7) a catalyst for olefin polymerization which comprises a transition metal compound represented by the above-mentioned general formula (1) or (II) and an activation cocatalyst, (8) a catalyst for olefin polymerization which comprises (A) a transition metal compound represented by the above-mentioned general formula (1) or (II) and (B) a compound capable of reacting with the transition metal compound of the component (A) or its derivative to form an ionic complex, (9) a catalyst for olefin polymerization which comprises (A) a transition metal compound represented by the above-mentioned general formula (1) or (II), (B) a compound capable of reacting with the transition metal compound of the component (A) or its derivative to form an ionic complex, and (C) an organic aluminum compound,

(10) an olefin polymer obtained by the use of a polymerization catalyst of the above-mentioned (7) to (9), and

(11) a process for preparing an olefin polymer which comprises the step of copolymerizing an olefin, another olefin and/or another monomer in the presence of a catalyst for olefin polymerization of the above-mentioned (7) to (9).

BEST MODE FOR CARRYING OUT THE INVENTION

A transition metal compound of the present invention is a novel multiple crosslinking type compound represented by the general formula (I):

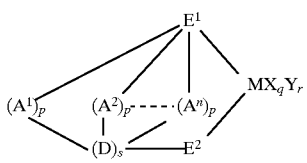 (I)

In the above-mentioned general formula (I), M is a metallic element in the groups 3 to 10 or a lanthanoide series of the periodic table, and typical examples of M include titanium, zirconium, hafnium, yttrium, vanadium, chromium, manganese, nickel, cobalt, palladium and lanthanoide metals. Above all, titanium, zirconium and hafnium are preferable from the viewpoint of an olefin polymerization activity. $E^1$ and $E^2$ are each a σ-bonding or a π-bonding ligand, and they form a crosslinking structure via $(A^1)_p$, $(A^2)_p$, ... $(A^n)_p$ and (D)s and may be the same or different. Typical examples of $E^1$ include a cyclopentadienyl group, a substituted cyclopentadienyl group, an indenyl group, a substituted indenyl group, a heterocyclopentadienyl group, a substituted heterocyclopentadienyl group, an amido group (—N<), a phosphide group (—P<), a hydrocarbon group (>CR— or >C<), a silicon-containing group (>SiR— or >Si<) (wherein R is hydrogen, a hydrocarbon group having 1 to 20 carbon atoms, or a hetero-atom-containing group). Typical examples of $E^2$ include a cyclopentadienyl group, a substituted cyclopentadienyl group, an indenyl group, a substituted indenyl group, a heterocyclopentadienyl group, a substituted heterocyclopentadienyl group, an amido group (—N<or — NR—), a phosphide group (—P< or —PR—), oxygen (—O—), sulfur (—S—), selenium (—Se—), a hydrocarbon group (>C(R)$_2$—, >CR— or >C<), a silicon-containing group (>SiR—, >Si(R)$_2$— or >Si<) (wherein R is hydrogen, a hydrocarbon group having 1 to 20 carbon atoms, or a hetero-atom-containing group).

Furthermore, X is a σ-bonding ligand, and when a plurality of Xs are present, these plural Xs may be the same or different, and each X may crosslink with another X, $E^1$, E2 or Y. Typical examples of X include a halogen atom, a hydrocarbon group having 1 to 20 carbon atoms, an alkoxy group having 1 to 20 carbon atoms, an aryloxy group having 6 to 20 carbon atoms, an amido group having 1 to 20 carbon atoms, a silicon-containing group having 1 to 20 carbon atoms, a phosphide group having 1 to 20 carbon atoms, a sulfide group having 1 to 20 carbon atoms and an acyl group having 1 to 20 carbon atoms. On the other hand, Y is a Lewis base, and when a plurality of Ys are present, these plural Ys may be the same or different, and each Y may crosslink with another Y, $E^1$, $E^2$ or X. Typical examples of the Lewis base which is represented by Y include an amine, an ether, a phosphine and a thioether.

Next, $A^1, A^2, \ldots A^n$ are each a crosslinking group and they may be the same or different, but at least one of them comprises a crosslinked structure consisting of carbon alone. Here, "at least one of them comprises a crosslinked structure consisting of carbon alone" means that at least one of them comprises a crosslinked structure represented by the general formula

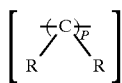

wherein R is a hydrogen atom, a halogen atom, a hydrocarbon group having 1 to 20 carbon atoms, a halogen-containing hydrocarbon group having 1 to 20 carbon atoms, a silicon-containing group or a hetero-atom-containing group, and plural Rs may be the same or different and may bond to each other to form a ring structure; and p is an integer of 1 to 4.

Typical examples of the crosslinking group include methylene, ethylene, ethylidene, isopropylidene, cyclohexylidene, 1,2-cyclohexylene and vinylidene (CH$_2$=C=).

Other typical structures of $A^1, A^2, \ldots A^n$ include R'$_2$Si, R'$_2$Ge, R'$_2$Sn, R'Al, R'P, R'P (=O), R'N, oxygen (—O—), sulfur (—S—) and selenium (—Se—) wherein R' is a hydrogen atom, a halogen atom, a hydrocarbon group having 1 to 20 carbon atoms, a halogen-containing hydrocarbon group having 1 to 20 carbon atoms, a silicon-containing group or a hetero-atom-containing group, and when two Rs are present, they may be the same or different and may bond to each other to form a ring structure. Typical examples of these crosslinking groups include dimethylsilylene, tetramethyldisilylene, dimethylgermylene, dimethylstannylene, methylborilidene (CH$_3$—B<), methylalumilidene (CH$_3$—Al<), phenylphosphilidene (Ph-P<), phenylphospholidene

(PhP<), methylimide, oxygen (—O—), sulfur (—S—) and selenium (—Se—). In addition, examples of $A^1, A^2, \ldots A^n$ include vinylene (—CH=CH—), o-xylylene

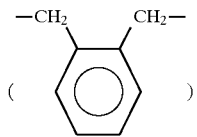

and 1,2-phenylene.

D represents a crosslinking group, and when a plurality of Ds are present, these plural Ds may be the same or different. Typical examples of D include R"C, R"Si, R"Ge, R"Sn, B, Al, P, P(=O) and N wherein R" is a hydrogen atom, a halogen atom, a hydrocarbon group having 1 to 20 carbon atoms, a halogen-containing hydrocarbon group having 1 to 20 carbon atoms, a silicon-containing group or a hetero-atom-containing group. Furthermore, n is an integer of 2 to 4; p is an integer of 1 to 4, and the respective ps may be the same or different; q is an integer of 1 to 5 [(the valence of M)–2]; r is an integer of 0 to 3; and s is an integer of 0 to 4, and when s is 0, $(A^1)_p, (A^2)_p, \ldots (A^n)_p$ and $E^2$ form a direct bond.

Of the compounds represented by the above-mentioned general formula (I), a transition metal compound represented by the following general formula (II) is preferable in which s is 0, i.e., any crosslinking group of D is not present:

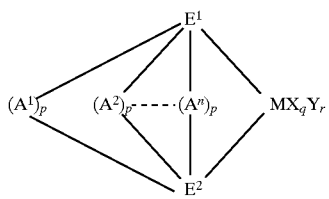 (II)

wherein M, $E^1, E^2$, X, Y, $A^1, A^2, \ldots A^n$, n, p, q and r are as defined above.

Typical examples of such a transition metal compound include (1,1'-dimethylsilylene)(2,2'-isopropylidene)-bis(cyclopentadienyl)zirconium dichloride, (1,1'- dimethylsilylene)(2,2'-isopropylidene)-bis(cyclopentadienyl)zirco-niumdimethyl, (1,1'-dimethylsilylene)(2,2'-isopropylidene)-bis(cyclopentadienyl)zirconiumdibenzyl, (1,1'-dimethylsilylene)(2,2'-isopropylidene)-bis(cyclopentadienyl)zirco-niumbis(trimethylsilyl), (1,1'-dimethylsilylene)(2,2'-isopropylidene)-bis(cyclopentadienyl)zirconiumbis(tri-methylsilylmethyl), (1,1'-dimethylsilylene)(2,2'-isopropylidene)-bis(cyclopentadienyl)zirconium dimethoxide, (1,1'-dimethylsilylene)(2,2'-isopropylidene)-bis(cyclopentadienyl)zirconiumbis(trifluoromethane sulfonate), (1,1'-dimethylsilylene)(2,2'-methylene)-bis(cyclopentadienyl)zirconium dichloride, (1,1'-ethylene)(2,2'-methylene)-bis(cyclopentadienyl)zirconium dichloride, (1,2'-dimethylsilylene)(2,1'-ethylene)-bis(indenyl)zirconium dichloride, (1,1'-dimethylsilylene)(2,2'-ethylene)-bis(indenyl)zirconium dichloride, (1,1'-ethylene)(2,2'-dimethylsilylene)-bis(indenyl)zirconium dichloride, (1,1'-dimethylsilylene)(2,2'-cyclohexylidene)-bis(indenyl)zirconium dichloride, (1,2'-dimethyl-silylene)(2,1'-isopropylidene)-bis(indenyl)zirconium dichloride, (1,1'-isopropylidene)(2,2'-dimethylsilylene)-bis(indenyl)zirconium dichloride, (1,1'-dimethylsilyl-ene)(2,2'-isopropylidene)-bis(indenyl)zirconium dichloride, (1,1'-dimethylsilylene)(2,2'-isopropylidene)-bis(indenyl)zirconium dimethyl, (1,1'-dimethylsilylene)(2,2'-isopropylidene)-bis(indenyl)zirconiumdibenzyl, (1,1'-dimethylsilyl-ene)(2,2'-isopropylidene)-bis(indenyl)zirconiumbis(tri-methylsilyl), (1,1'-dimethylsilylene)(2,2'-isopropylidene)-bis(indenyl)zirconiumbis(trimethylsilylmethyl), (1,1'-dimethylsilylene)(2,2'-isopropylidene)-bis(indenyl)zirconium dimethoxide, (1,1'-dimethylsilylene)(2,2'-isopropylidene)-bis(indenyl)zirconiumbis(trifluoromethane sulfonate), (1,1'-dimethylsilylene)(2,2'-isopropylidene)-bis(4,5,6,7-tetrahydroindenyl)zirconium dichloride, (1,2'-ethylene)(2,1'-isopropylidene)-bis(indenyl)zirconium dichloride, (1,1'-ethylene)(2,2'-isopropylidene)-bis(indenyl)-zirconium dichloride, (1,1'-isopropylidene)(2,2'-ethylene)-bis(indenyl)zirconium dichloride, (1,1'-isopropylidene)-(2,2'-isopropylidene)-bis(cyclopentadienyl)zirconium dichloride, (1,1'-dimethylsilylene)(2,2'-isopropylidene)-(3,4-dimethylcyclopentadienyl)(3',4'-dimethylcyclopentadienyl)-zirconium dichloride, (1,1'-dimethylsilylene)(2,2'-isopropylidene)-(4-methylcyclopentadienyl)(4'-methylcyclopentadienyl)zirconium dichloride, (1,1'-dimethylsilylene)(2,2'-isopropylidene)-(3,4,5-trimethylcyclopentadienyl)(3',4',5'-trimethylcyclopentadienyl)zirconium dichloride, (1,1'-dimethylsilylene)(2,2'-isopropylidene)-(4-n-butylcyclopentadienyl)(4'-n-butylcyclopentadienyl)zirconium dichloride, (1,1'-dimethylsilylene)(2,2'-isopropylidene)(4-tert-butylcyclopentadienyl)(4'-tert-butylcyclopentadienyl)zirco-nium dichloride, (1,2'-dimethylsilylene)(2,1'-isopropylidene)-(3-methylindenyl)(3'-methylindenyl)zirconium dichlo-ride, (1,1'-dimethylsilylene)(2,2'-isopropylidene)-(3-methylindenyl)(3'-methylindenyl)zirconium dichloride, (1,1'-isopropylidene)(2,2'-dimethylsilylene)-(3-methylindenyl)-(indenyl)zirconium dichloride, (1,1'-dimethylsilylene)(2,2'-isopropylidene)-(4,7-dimethylindenyl)(indenyl)zirconium dichloride, (1,1'-dimethylsilylene)(2,2'-isopropylidene)-(4,5-benzoindenyl)(indenyl)zirconium dichloride, (1,1'-dimethylsilylene)(2,2'-isopropylidene)-(4,7-dimethylindenyl)(4',7'-dimethylindenyl)zirconium dichloride, (1,1'-dimethylsilylene)(2,2'-isopropylidene)-(4,5-benzoindenyl)-(4,5-benzoindenyl)zirconium dichloride, (1,1'-dimethyl-silylene)(2,2'-isopropylidene)-(3-methylindenyl)(3'-methylindenyl)zirconium dichloride, (1,1'-dimethylsilylene)(2,2'-isopropylidene)-(3-ethylindenyl)(3'-ethylindenyl)zirconium dichloride, (1,1'-dimethylsilylene)(2,2'-isopropylidene)-(3-n-butylindenyl)(3'-n-butylindenyl)zirconium dichloride, (1,1'-dimethylsilylene)(2,2'-isopropylidene)-(3-tert-butylindenyl)(3'-tert-butylindenyl)zirconium dichloride, (1,1'-dimethylsilylene)(2,2'-isopropylidene)-(3-trimethylsilylindenyl)(3'-trimethylsilylindenyl)zirconium dichloride, (1,1'-dimethylsilylene)(2,2'-isopropylidene)-(3-benzylindenyl)(3'-benzylindenyl)zirconium dichloride, (1,1'-dimethylsilylene)(2,2'-ethylene)-(indenyl)(cyclopenta-dienyl)zirconium dichloride, (1,1'-dimethylsilylene)(2,2'-isopropylidene)-(indenyl)(cyclopentadienyl)zirconium dichloride, (3,3'-isopropylidene)(4,4'-isopropylidene)-(1-phosphacyclopentadienyl)(1'-phosphacyclopentadienyl)-zirconium dichloride, (3,1'-isopropylidene)(4,2'-isopropylidene)-(1phosphacyclopentadienyl)(4'-cyclopentadienyl)zirconium dichloride, these compounds in which zirconium is replaced with titanium, and these compounds in which zirconium is replaced with hafnium. Needless to say, they are not restrictive. In addition, similar compounds containing metallic elements in other groups and a lanthanoide series of the periodic table are also usable.

The present invention is also directed to a multiple crosslinking type bisindenyl derivative represented by the general formula (III)

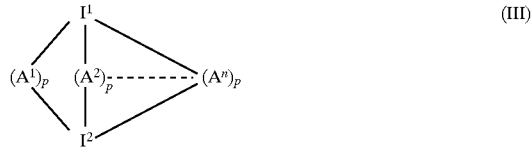

(III)

wherein $I^1$ and $I^1$ are each an indenyl group or a substituted indenyl group, and $A^1, A^2, \ldots A^n$, n and p are as defined above, and this bisindenyl derivative can be used as a ligand in the transition metal compound represented by the general formula (II).

Typical examples of the multiple crosslinking type bisindenyl derivative represented by the general formula (III) include (1,2'-dimethylsilylene)(2,1'-ethylene)-bis(indene), (1,1'-dimethylsilylene)(2,2'-ethylene)-bis(indene), (1,1'-ethylene)(2,2'-dimethylsilylene)-bis(indene), (1,2'-dimethylsilylene)(2,1'-isopropylidene)-bis(indene), (1,1'-isopropylidene)(2,2'-dimethylsilylene)-bis(indene), (1,1'-dimethylsilylene)(2,2'-isopropylidene)-bis(indene), (1,2'-ethylene)(2,1'-isopropylidene)-bis(indene), (1,1'-ethylene)(2,2'-isopropylidene)-bis(indene), (1,1'-isopropylidene)(2,2'-ethylene)-bis(indene), (1,1'-dimethylsilylene)(2,2'-cyclohexylidene)-bis(indene), (1,2'-dimethylsilylene)(2,1'-isopropylidene)-(3-methylindene)(3'-methylindene), (1,1'-dimethylsilylene)(2,2'-isopropylidene)-(3-methylindene)(3'-methylindene), (1,1'-isopropylidene)-(2,2'-dimethylsilylene)-(3-methylindene)(indene), (1,1'-dimethylsilylene)(2,2'-isopropylidene)-(4,7-dimethylindene)(indene), (1,1'-dimethylsilylene)(2,2'-isopropylidene)-(4,5-benzoindene)(indene), (1,1'-dimethylsilylene)(2,2'-isopropylidene)-(4,7-dimethylindene)(4',7'-dimethylindene), (1,1'-dimethylsilylene)(2,2'-isopropylidene)-(4,5-benzoindene)(4,5-benzoindene), (1,1'-dimethylsilylene)(2,2'-isopropylidene)-(3-methylindene)(3'-methylindene), (1,1'- dimethylsilylene)(2,2'-isopropylidene)-(3-methylindene)(3'-ethylindene), (1,1'-dimethylsilylene)(2,2'-isopropylidene)-(3-n-butylindene)(3'-n-butylindene), (1,1'-dimethylsilylene)(2,2'-isopropylidene)-(3-tert-butylindene)(3'-tert-butylindene), (1,1'-dimethylsilylene)(2,2'-isopropylidene)-(3-trimethylsilylindene)(3'-trimethylsilylindene), (1,1'-dimethylsilylene)(2,2'-isopropylidnene)-(3-benzylindene)(3'-benzylindene), (1,1'-dimethylsilylene)(2,2'-ethylene)-(indene)(cyclopentadiene) and (1,1'-dimethylsilylene)(2,2'-isopropylidene)-(indene)(cyclopentadiene).

Furthermore, the transition metal compound represented by the general formula (II) of the present invention can be prepared by any of various methods, but according to a process of the present invention, it can easily be prepared as follows.

In the first place, a compound represented by the general formula (IV)

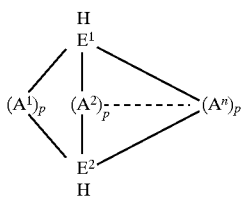
(IV)

wherein $E^1$, $E^2$, $A^1$, $A^2$, ... $A^n$, n and p are as defined above,
is dimetallized with a compound represented by the general formula (XI)

$$R^8M^1 \tag{XI}$$

wherein $R^8$ is a conjugated base in which an acid dissociation constant (pKa value) is 25 or more in terms of $R^8$-H; and $M^1$ is an alkali metal, an alkaline earth metal-containing salt residue or an organic aluminum residue, in a suitable solvent, for example, an ether such as diethyl ether, diisopropyl ether, di-n-butyl ether, 1,2-diethoxyethane, 1,2-dimethoxyethane or tetrahydrofuran, or a hydrocarbon such as n-hexane, n-pentane, n-octane, benzene, toluene or xylene to obtain a compound represented by the general formula (V)

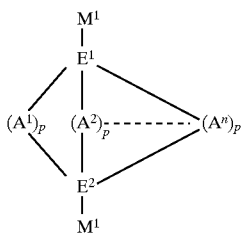
(V)

wherein $M^1$, $E^1$, $E^2$, $A^1$, $A^2$, ... $A^n$, n and p are as defined above.

In the above-mentioned general formula (XI), as $R^8$, a conjugated base in which an acid dissociation constant (pKa value) is 30 or more in terms of $R^8$-H is particularly preferable from the viewpoint of a production efficiency, and typical examples of $R^8$ include amides such as diisopropylamide, diethylamide, dimethylamide, piperidide and pyrrolidide, and hydrocarbon anions having 1 to 20 carbon atoms such as a phenyl anion, a methyl anion, an n-butyl anion, a cyclohexyl anion, a benzyl anion, a vinyl anion and an allyl anion.

Furthermore, $M^1$ is an alkali metal, an alkaline earth metal-containing salt residue or an organic aluminum residue, and examples of the alkali metal include lithium, sodium and potassium. An example of the alkaline earth metal-containing salt residue is a compound represented by $MgX^1$ ($X^1$ is a halogen atom such as bromine, iodine or chlorine), and an example of the organic aluminum residue is a compound represented by $AlR'''_2$ ($R'''$ is a hydrocarbon group having 1 to 20 carbon atoms, and two $R'''$'s may be the same or different). The concentration of a compound represented by the above-mentioned general formula (IV) is advantageously in the range of 0.01 to 5 mol/liter, preferably 0.1 to 3 mol/liter. No particular restriction is put on a reaction temperature of this dimetallization, and the reaction temperature is selected in the range of from a solidifying point of the solvent to a boiling point of the solvent, but it is preferably within the range of −100° to 100° C., more preferably −80° to 30° C. In addition, the reaction temperature does not always have to be maintained at a constant temperature. No particular restriction is put on a mixing order of the material compounds, and the compound represented by the general formula (XI) may be added to the compound represented by the general formula (IV) and vice versa, but the former is preferable. With regard to a use ratio between the compound represented by the general formula (IV) and the compound represented by the general formula (XI), it is preferred to use the compound represented by the general formula (XI) in a ratio of 1 to 4 mol, preferably 1.8 to 2.2 mol with respect to 1 mol of the compound represented by the general formula (IV).

Next, the thus obtained compound represented by the general formula (V) is then reacted with a compound represented by the general formula (VI)

$$Mx_{q+2} \tag{VI}$$

wherein M, X and q are as defined above),
in a suitable solvent such as the above-mentioned solvent and, if necessary, in the presence of a Lewis base, thereby obtaining a transition metal compound represented by the general formula (II).

Examples of the compound represented by the above-mentioned general formula (VI) include $TiCl_4$, $TiBr_4$, $ZrCl_4$, $HfCl_4$, $YCl_3$, $ScCl_3$, $M'Cl_3$ (M' is a lanthanoide metal), $VCl_3$, $NbCl_5$, $TaCl_5$, $CrCl_3$, $MoCl_5$, $WCl_6$, $FeCl_2$, $RuCl_2$, $NiCl_2$ and $PdCl_2$.

With regard to a use ratio between the compound represented by the general formula (V) and the compound represented by the general formula (VI), it is preferred to use the compound represented by the general formula (VI) in a ratio of 0.1 to 10 mol, preferably 0.5 to 2 mol with respect to 1 mol of the compound represented by the general formula (V). No particular restriction is put on a mixing order of both the compounds. In addition, the solvent, concentration and temperature in this reaction are the same as in the case of the dimetallizing reaction of the compound represented by the general formula (IV).

According to an alternative method, 1 mol of the compound represented by the general formula (V) is reacted with about 1 to 4 mol, preferably about 1.8 to 2.2 mol of tin trialkylhalide, silicon trialkylhalide or germanium trialkylhalide to replace $M^1$ with another metal containing an organic group such as trialkyltin, trialkylsilicon or trialkylgermanium, or the compound represented by the general formula (V) is reacted with about 1 to 4 mol, preferably about 1.8 to 2.2 mol of an alkoxythallium to replace $M^1$ with thallium (first reaction); and this compound, in which $M^1$ is replaced with the other metal containing the organic group or thallium, is then reacted with the compound represented by the general formula (VI) in a ratio of about 1 to 4 mol, preferably about 1.8 to 2.2 mol of the latter to 1 mol of the former, if necessary, in the presence of a Lewis base (second reaction), thereby obtaining the transition metal compound represented by the general formula (II). In this reaction, no particular restriction is put on a mixing order of the compounds in both the first reaction and the second reaction. In addition, the solvent, concentration and temperature in the first reaction are the same as in the case of the dimetallizing reaction of the compound represented by the general formula (IV). In the second reaction, halogenated hydrocarbons such as dichloromethane and chloroform as well as a nitrile such as acetonitrile can be used as the solvent in addition to the above-mentioned solvents. The concentration and temperature in the second reaction are the same as in the case of the dimetallizing reaction of the compound represented by the general formula (IV).

Furthermore, the present invention is also directed to a bisindenyl derivative represented by the following general formula (VII) which is useful as a precursor of a multiple crosslinking type bisindenyl derivative represented by the above-mentioned general formula (III) usable as a ligand in the transition metal compound, and a process for preparing the bisindenyl derivative:

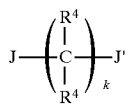

(VII)

wherein J and J' are each a group represented by the formula

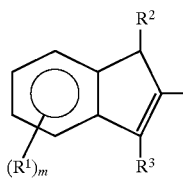

(wherein $R^1$, $R^2$ and $R^3$ are each a hydrogen atom, a hydrocarbon group having 1 to 20 carbon atoms, or a silicon-containing, an oxygen-containing or a halogen-containing group, and they may be the same or different, and when a plurality of $R^1$s are present, these plural $R^1$s may be the same or different and may bond to each other to form a ring structure, and $R^1$ and $R^2$ or $R^1$ and $R^3$ may bond to each other to form a ring structure; and m is an integer of 1 to 4), and J and J' may be the same or different; $R^4$ is a hydrogen atom, a hydrocarbon group having 1 to 20 carbon atoms, or a silicon-containing, an oxygen-containing or a halogen-containing group, and a plurality of $R^4$s may be the same or different, and they may be the same or different and may bond to each other to form a ring structure; and k is an integer of 1 to 20, but when k is 1 or 2, at least one of $R^4$s is not the hydrogen atom.

Next, the process for preparing the bisindenyl derivative represented by the general formula (VII) will be described. A mixture comprising one or two of compounds represented by the general formula (VIII)

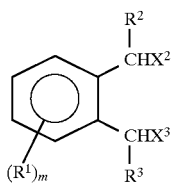

(VIII)

wherein $X^2$ and $X^3$ are each a halogen atom, and they may be the same or different; and $R^1$, $R^2$, $R^3$ and m are as defined above, is reacted with an alkali metal or an alkaline earth metal at a temperature in the range of −50° to 100° C., preferably 0° to 70° C. (however, when the boiling point of the solvent is lower than this temperature, this boiling point is regarded as an upper limit) in a suitable organic solvent, for example, an ether such as diethyl ether, diisopropyl ether, di-n-butyl ether, 1,2-diethoxyethane, 1,2-dimethoxyethane or tetrahydrofuran, or a hydrocarbon such as n-pentane, n-octane, n-hexane, toluene or xylene, thereby obtaining a compound represented by the general formula (XII)

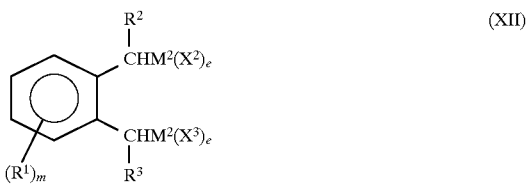

wherein $M^2$ is an alkali metal or an alkaline earth metal; e is 0 in the case that $M^2$ is the alkali metal or 1 in the case that $M^2$ is the alkaline earth metal; and $R^1$, $R^2$, $R^3$, $X^2$ and $X^3$ and m are as defined above.

In this case, a preferable example of the alkali metal is lithium, potassium or sodium, and an preferable example of the alkaline earth metal is magnesium. A molar ratio of the compound represented by the general formula (XIII) to the above-mentioned metal is in the range of 0.25 to 16, preferably 0.5 to 8. Moreover, no particular restriction is put on a mixing order of these materials.

Furthermore, the concentration of the compound represented by the general formula (XII) is preferably in the range of 0.01 to 5 mol/liter, preferably 0.1 to 3 mol/liter. If this concentration is less than 0.01 mol/liter, a volume efficiency is low and productivity is also low, and if it is more than 5 mol/liter, the production efficiency of the compound represented by the general formula (XII) deteriorates.

Next, a compound represented by the general formula (IX)

wherein $Y^1$ and $Y^2$ is each $OR^5$, $NR^6_2$, $SR^7$ (wherein $R^5$ to $R^7$ are each a hydrogen atom, a hydrocarbon group having 1 to 20 carbon atoms, or a silicon-containing, an oxygen-containing or a halogen-containing group) or a halogen atom, and they may be the same or different; $Y^3$ and $Y^4$ are each O, S or $NR^8$ (wherein $R^8$ is a hydrogen atom, a hydrocarbon group having 1 to 20 carbon atoms, or a silicon-containing, an oxygen-containing or a halogen-containing group), and they may be the same or different; and $R^4$ and k are as defined above, is added to the reaction solution containing the compound represented by the general formula (XII) without isolating the compound therefrom, and the compound of the general formula (IX) is reacted with the compound of the general formula (XII) at a temperature of −100° to 100° C., preferably −80° to 50° C., thereby obtaining a compound represented by the general formula (X)

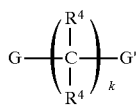

(X)

wherein G and G' are each a group represented by the general formula

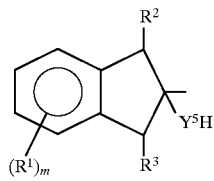

and G and G' may be the same or different; and $R^4$ and k are as defined above.

In this reaction, no particular restriction is put on the concentration of the compound represented by the general formula (X) in the reaction solution. A molar ratio of the compound represented by the general formula (XII) to the compound represented by the general formula (IX) is suitably within the range of 1 to 10, preferably 2 to 4. Moreover, no particular restriction is put on a mixing order of these compounds.

Furthermore, the thus obtained compound represented by the general formula (X) is dehydrated in a suitable solvent to obtain the bisindenyl derivative represented by the general formula (VII).

No particular restriction is put on the solvent for use in this dehydrating reaction, and any solvent can be used, so far as it can dissolve the compound represented by the general formula (X) and it is inert to the reaction. In addition, in this dehydrating reaction, a Brønsted acid or a Lewis acid is usually used. Here, as the Brønsted acid, there can preferably be used an acid having an acid dissociation constant (pKa value) of –6 or less, and examples of such an acid include hydrochloric acid, sulfuric acid, perchloric acid and p-toluenesulfonic acid. On the other hand, examples of the Lewis acid include $I_2$, $AlCl_3$, $AlBr_3$, $MgCl_2$, $ZnCl_2$, $ZnI_2$, $ZnBr_2$, $SnCl_4$, $TiCl_4$, $ZrCl_1$, $HfCl_4$, $YCl_3$, $FeCl_3$ and $CuCl_2$. No particular restriction is put on the amount of the Brønsted acid or the Lewis acid to be used, and the amount may be a catalytic amount.

The temperature of the dehydrating reaction is usually selected in the range of –100° to 300° C., preferably 0° to 100° C.

Of the bisindenyl derivatives represented by the above-mentioned general formula (VII), the bisindenyl derivatives in which k is 1 are preferable.

Typical examples of the bisindenyl derivatives represented by the above-mentioned general formula (VII) include (2,2'-isopropylidene)-bis(indene), (2,2'-isopropylidene)-(3-methylindene)(3'-methylindene), (2,2'-isopropylidene)-(3-methylindene)(indene), (2,2'-isopropylidene)(4,7-dimethylindene)(indene), (2,2'-isopropylidene)-(4,5-benzoindene)(indene), (2,2'-isopropylidene)-(4,7-dimethylindene), (4',7'-dimethylindene), (2,2'-isopropylidene)-(4,5-benzoindene) (4,5-benzoindene), (2,2'-isopropylidene)-(3-methylindene)(3'-methylindene), (2,2'-isopropylidene)-(3-ethylindene)(3'-methylindene), (2,2'-isopropylidene)-(3-n-butylindene)(3'-n-butylindene), (2,2'-isopropylidene)-(3-tert-butylindene)(3'-tert-butylindene), (2,2'-isopropylidene)-(3-trimethysilylindene)(3'-trimethylsilylindene), (2,2'-isopropylidene)-(3-benzylindene)(3'-benzylindene) and (2,2'-cyclohexylidene)-bis(indene).

The catalyst for olefin polymerization of the present invention is a catalyst comprising (A) the transition metal compound represented by the general formula (I) or (II), an activation cocatalyst, for example, (B) a compound capable of reacting with the transition metal compound of the component (A) or its derivative to form an ionic complex, and if necessary, (C) an organic aluminum compound.

In this catalyst for polymerization, the transition metal compounds represented by the general formula (I) and (II), which can be used as the component (A), may be used singly or in a combination of two or more thereof.

In this catalyst for polymerization of the present invention, the component (A) and the activation cocatalyst are used. No particular restriction is put on the activation cocatalyst, but for example, as the component (B), there can be used a compound capable of reacting with the transition metal compound of the component (A) or its derivative to form an ionic complex.

As examples of this component (B), an ionic compound (B-1) capable of reacting with the transition metal compound of the component (A) to form an ionic complex, an aluminoxane (B-2) or a Lewis acid (B-3) are preferable, because they have a high polymerization activity and can reduce a catalyst cost.

As the component (B-1), any compound can be used, so far as it can react with the transition metal compound of the component (A) to form an ionic complex, but compounds represented by the following general formulae (XIII) and (XIV) can be suitably used from the viewpoints of the particularly efficient formation of activation points for the polymerization and the like:

 (XIII)

 (XIV)

wherein $L^2$ is $M^4$, $R^{10}R^{11}M^5$, $R^{12}{}_3C$ or $R^{13}M^5$; $L^1$ is a Lewis base; $[Z]^-$ is a non-coordinating anion $[Z^1]^-$ or $[Z^2]^-$; here $[Z^1]^-$ is an anion in which a plurality of groups are bonded to an element, i.e., $[M^3G^1G^2 \ldots G^f]$ wherein $M^3$ is an element in the groups 5 to 15, preferably the groups 13 to 15 of the periodic table; $G^1$ to $G^f$ are each a hydrogen atom, a halogen atom, an alkyl group having 1 to 20 carbon atoms, a dialkylamino group having 2 to 40 carbon atoms, an alkoxy group having 1 to 20 carbon atoms, an aryl group having 6 to 20 carbon atoms, an aryloxy group having 6 to 20 carbon atoms, an alkylaryl group having 7 to 40 carbon atoms, an arylalkyl group having 7 to 40 carbon atoms, a halogen-substituted hydrocarbon group having 1 to 20 carbon atoms, an acyloxy group having 1 to 20 carbon atoms, an organic metalloid group or a hetero-atom-containing hydrocarbon group having 2 to 20 carbon atoms, and two or more of $G^1$ to $G^f$ may form a ring; f is an integer of [(a valence of the central metal $M^3$)+1]; $[Z^2]^-$ is a Brønsted acid single in which a logarithm (pKa) of a reciprocal number of an acid dissociation constant is –10 or less, a conjugated base of a combination of the Brønsted acid and a Lewis acid, or a conjugated base usually defined as a superstrong acid, and $[Z^2]^-$ may be coordinated with a Lewis base; $R^9$ is a hydrogen atom, an alkyl group having 1 to 20 carbon atoms, an aryl group, an alkylaryl group or an arylalkyl group having 6 to 20 carbon atoms; $R^{10}$ and $R^{11}$ are each a cyclopentadienyl group, a substituted cyclopentadienyl group, an indenyl group or a fluorenyl group; $R^{12}$ is an alkyl group, an aryl group, an alkylaryl group or an arylalkyl group having 1 to 20 carbon atoms; $R^{13}$ is a large cyclic ligand such as tetraphenylporphyrin or phthalocyanine; h is an ionic valence of $[L^1-R^9]$ or $[L^2]$ and it is an integer of 1 to 3; a is an integer of 1 or more; b is (h×a); $M^4$ is an element in the groups 1 to 3, 11 to 13 and 17 of the periodic table; and $M^5$ is an element in the groups 7 to 12 of the periodic table.

Here, typical examples of $L^1$ include amines such as ammonia, methylamine, aniline, dimethylamine, diethylamine, N-methylaniline, diphenylamine, N,N-dimethylaniline, trimethylamine, triethylamine, tri-n-butylamine, methyldiphenylamine, pyridine, p-bromo-N,N-dimethylaniline and p-nitro-N,N-dimethylaniline, phosphines such as triethylphosphine, triphenylphosphine and diphenylphosphine, a thioether such as tetrahydrothiophene, an ester such as ethyl benzoate, and nitriles such as acetonitrile and benzonitrile.

Typical examples of $R^9$ include hydrogen, a methyl group, an ethyl group, a benzyl group and a trityl group, and typical examples of $R^{10}$ and $R^{11}$ include a cyclopentadienyl group, a methylcyclopentadienyl group, an ethylcyclopentadienyl group and a pentamethylcyclopentadienyl group. Typical examples of $R^{12}$ include a phenyl group, a p-tolyl group and a p-methoxyphenyl group, and typical examples of $R^{13}$ include tetraphenylporphine, phthalocyanine, allyl and methallyl. Typical examples of $M^4$ include Li, Na, K, Ag, Cu, Br, I and $I_3$, and typical examples of $M^5$ include Mn, Fe, Co, Ni or Zn.

Furthermore, typical examples of $M^3$ in $[Z^1]^-$, i.e., $[M^3G^1G^2 \ldots G^f]$ include B, Al, Si, P, As and Sb, and above all, B and Al are preferable. Typical examples of $G^1$, $G^2$ to $G^f$ include dialkylamino groups such as a dimethylamino group and a diethylamino group, alkoxy groups and aryloxy groups such as a methoxy group, an ethoxy group, an n-butoxy group and a phenoxy group, hydrocarbon groups such as a methyl group, an ethyl group, an n-propyl group, an isopropyl group, an n-butyl group, an isobutyl group, an n-octyl group, an n-eicosyl group, a phenyl group, a p-tolyl group, a benzyl group, a 4-t-butylphenyl group and a 3,5-dimethylphenyl group, halogen atoms such as fluorine, chlorine, bromine and iodine, hetero-atom-containing hydrocarbon groups such as a p-fluorophenyl group, a 3,5-difluorophenyl group, a pentachlorophenyl group, a 3,4,5-trifluorophenyl group, a pentafluorophenyl group, a 3,5-bis(trifluoromethyl)phenyl group and a bis(trimethylsilyl)methyl group, and organic metalloid groups such as a pentamethylantimony group, a trimethylsilyl group, a trimethylgermyl group, a diphenylarsine group, a dicyclohexylantimony group and a diphenylboron group.

Typical examples of the non-coordinating anion, i.e., the conjugated base $[Z^2]^-$ which is the Brønsted acid single having a pKa of −10 or less or the combination of the Brønsted acid and the Lewis acid include trifluoromethanesulfonic acid anion $(CF_3SO_3)^-$, bis(trifluoromethanesulfonyl)methyl anion, bis(trifluoromethanesulfonyl)benzyl anion, bis(trifluoromethanesulfonyl)amide, perchloric acid anion $(ClO_4)^-$, trifluoroacetic acid anion $(CF_3CO_2)^-$, hexafluoroantimony anion $(SbF_6)^-$, fluorosulfonic acid anion $(FSO_3)^-$, chlorosulfonic acid anion $(ClSO_3)^-$, fluorosulfonic acid anion-5-antimony fluoride $(FSO_3\text{-}SbF_5)^-$, fluorosulfonic acid anion-5-arsenic fluoride $(FSO_3\text{-}AsF_5)^-$ and trifluoromethanesulfonic acid-5-antimony fluoride $(CF_3SO_3\text{-}SbF_5)^-$.

Typical examples of the ionic compound, i.e., the (B-1) component compound capable of reacting with the transition metal compound of the above-mentioned component (A) to form an ionic complex include triethylammonium tetraphenylborate, tri-n-butylammonium tetraphenylborate, trimethylammonium tetraphenylborate, tetraethylammonium tetraphenylborate, methyl(tri-n-butyl)ammonium tetraphenylborate, benzyl(tri-n-butyl)ammonium tetraphenylborate, dimethyldiphenylammonium tetraphenylborate, triphenyl(methyl)ammonium tetraphenylborate, trimethylanilinium tetraphenylborate, methylpyridinium tetraphenylborate, benzylpyridinium tetraphenylborate, methyl(2-cyanopyridinium) tetraphenylborate, triethylammonium tetrakis(pentafluorophenyl)borate, tri-n-butylammonium tetrakis(pentafluorophenyl)borate, triphenylammonium tetrakis(pentafluorophenyl)borate, tetra-n-butylammonium tetrakis(pentafluorophenyl)borate, tetraethylammonium tetrakis(pentafluorophenyl)borate, benzyl(tri-n-butyl)ammonium tetrakis(pentafluorophenyl)borate, methyldiphenylammonium tetrakis(pentafluorophenyl)borate, triphenyl(methyl) ammonium tetrakis(pentafluorophenyl)borate, methylanilinium tetrakis(pentafluorophenyl)borate, dimethylanilinium tetrakis(pentafluorophenyl)borate, trimethylanilinium tetrakis(pentafluorophenyl)borate, methylpyridinium tetrakis(pentafluorophenyl)borate , benzylpyridinium tetrakis(pentafluorophnlurophenyl)borate, methyl(2-cyanopyridinium) tetrakis(pentafluorophenyl)borate, benzyl(2-cyanopyridinium) tetrakis(pentafluorophenyl)borate, methyl(4-cyanopyridinium) tetrakis(pentafluorophenyl)borate, triphenylphosphonium tetrakis(pentafluorophenyl)borate, dimethylanilinium tetrakis[bis(3,5-ditrifluoromethyl)phenyl]borate, ferrocenium tetraphenylborate, silver tetraphenylborate, trityl tetraphenylborate, tetraphenylporphyrinmanganese tetraphenylborate, ferrocenium tetrakis(pentafluorophenyl)borate, (1,1'-dimethylferrocenium) tetrakis(pentafluorophenyl)borate, decamethylferrocenium tetrakis(pentafluorophenyl)borate, silver tetrakis(pentafluorophenyl)borate, trityl tetrakis(pentafluorophenyl)borate, lithium tetrakis(pentafluorophenyl)borate, sodium tetrakis(pentafluorophenyl)borate, tetraphenylporphyrinmanganese tetrakis(pentafluorophenyl)borate, silver tetrafluoroborate, silver hexafluorophosphate, silver hexafluoroarsenate, silver perchlorate, silver trifluoroacetate and silver trifluoromethanesulfonate.

The ionic compounds, which can be used as the component (B-1), capable of reacting with the transition metal compound of the component (A) to form an ionic complex may be used singly or in a combination of two or more thereof.

On the other hand, examples of the aluminoxane which is the component (B-2) include a chain aluminoxane represented by the general formula (XV)

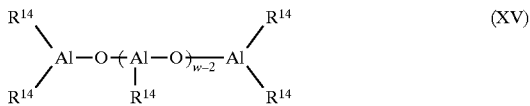

wherein $R^{14}$ is a hydrocarbon group such as an alkyl group, an alkenyl group, an aryl group or an arylalkyl group having 1 to 20 carbon atoms, preferably 1 to 12 carbon atoms or a halogen atom, and a plurality of $R^{14}S$ may be the same or different; and w is an average polymerization degree and it is usually an integer of 2 to 50, preferably 2 to 40, and a cyclic aluminoxane represented by the general formula (XVI)

wherein $R^{14}$ and w are the same as in the above-mentioned general formula (XV).

A method for preparing the above-mentioned aluminoxane comprises the step of bringing an alkylaluminum into contact with a condensing agent such as water, but its means is not particularly limited and a known procedure can be used to carry out a reaction. For example, there are (1) a method which comprises dissolving an organic aluminum compound in an organic solvent, and then bringing the solution into contact with water, (2) a method which comprises first adding an organic aluminum compound to a polymerization system at the time of polymerization, and then adding water, (3) a method which comprises reacting an organic aluminum compound with crystal water contained in a metallic salt or water adsorbed on an inorganic material or an organic material, and (4) a method which comprises reacting a tetraalkyldialuminoxane with trialkylaluminum, and then reacting the resultant reaction product with water. In this connection, the aluminoxane which is insoluble in toluene is also usable.

These aluminoxanes may be used singly or in a combination of two or more thereof.

No particular restriction is put on the Lewis acid which is the component (B-3), and it may be an organic compound or a solid inorganic compound. As the organic compound, a boron compound or an aluminum compound can preferably be used, and as the inorganic compound, a magnesium compound or an aluminum compound can preferably be used, because they can efficiently form activation points. Examples of the aluminum compound as the organic compound include bis(2,6-di-t-butyl-4-methylphenoxy) aluminummethyl and (1,1-bi-2-naphthoxy) aluminummethyl, and examples of the magnesium compound include magnesium chloride and diethoxymagnesium. Examples of the aluminum compound as the inorganic compound include aluminum oxide and aluminum chloride, and examples of the boron compound include triphenylboron, tris(pentafluorophenyl)boron, tris[3,5-bis-(trifluoromethyl)phenyl]boron, tris[(4-fluoromethyl)-phenyl]boron, trimethylboron, triethylboron, tri-n-butylboron, tris(fluoromethyl)boron, tris(pentafluoroethyl) boron, tris(nonafluorobutyl)boron, tris(2,4,6-trifluorophenyl)boron, tris(3,5-difluoro)boron, tris[3,5-bis (trifluoromethyl)phenyl]boron, bis(pentafluorophenyl) fluoroboron, diphenylfluoroboron, bis(pentafluorophenyl) chloroboron, dimethylfluoroboron, diethylfluoroboron, di-n-butyl-fluoroboron, pentafluorophenyldifluoroboron, phenyldifluoroboron, pentafluorophenyldichloroboron, methyldifloroboron, ethyldifluoroboron and n-butyldifluoroboron.

These Lewis acids may be used singly or in a combination of two or more thereof.

A molar ratio of the catalytic component (A) to the catalytic component (B) in the catalyst for polymerization of the present invention is preferably in the range of 10:1 to 1:100, more preferably 2:1 to 1:10 in the case that the compound (B-1) is used as the catalytic component (B), and if the molar ratio deviates from the above-mentioned range, the catalyst cost per unit weight of an obtained polymer increases, which is not practical. In the case that the compound (B-2) is used, the molar ratio is preferably in the range of 1:1 to 1:1000000, more preferably 1:10 to 1:10000. If the molar ratio deviates from the above-mentioned range, the catalyst cost per unit weight of an obtained polymer increases, which is not practical.

A molar ratio of the catalytic component (A) to the catalytic component (B-3) is preferably in the range of 10:1 to 1:2000, more preferably 5:1 to 1:1000, most preferably 2:1 to 1:500, and if the molar ratio deviates from the above-mentioned range, the catalyst cost per unit weight of an obtained polymer increases, which is not practical.

Furthermore, as the catalytic component (B), the compounds (B-1), (B-2) and (B-3) may be used singly or in a combination of two or more thereof.

The catalyst for polymerization of the present invention may contain the above-mentioned components (A) and (B) as the main components, or alternatively, it may contain the components (A) and (B) as well as an organic aluminum compound (C) as the main components.

Here, as the organic aluminum compound of the component (C), there can be used a compound represented by the general formula (XVII)

$$R^{15}_v AlQ_{3-v} \qquad (XVII)$$

wherein $R^{15}$ is an alkyl group having 1 to 10 carbon atoms; Q is a hydrogen atom, an alkoxy group having 1 to 20 carbon atoms, an aryl group having 6 to 20 carbon atoms or a halogen atom; and v is an integer of 1 to 3.

Typical examples of the compound represented by the general formula (XVII) include trimethylaluminum, triethylaluminum, triisopropylaluminum, triisobutylaluminum, dimethylaluminum chloride, diethylaluminum chloride, methylaluminum dichloride, ethylaluminum dichloride, dimethylaluminum fluoride, diisoblutylaluminum hydride, diethylaluminum hydride and ethylaluminum sesquichloride.

These organic aluminum compounds may be used singly or in a combination of two or more thereof.

A molar ratio of the catalytic component (A) to the catalytic component (C) is preferably in the range of 1:1 to 1:10000, more preferably 1:5 to 1:2000, most preferably 1:10 to 1:1000. The employment of the catalytic component (C) enables a polymerization activity per transition metal to improve, but if the amount of the catalytic component (C) is excessively large, particularly if it is in excess of the above-mentioned range, the organic aluminum compound is used in vain and it remains in large quantities in the polymer. Conversely, if it the amount of the catalytic component (C) is small, a sufficient catalytic activity cannot be obtained unpreferably sometimes.

In the present invention, at least one of the catalytic components, when used, may be supported on a suitable carrier. No particular restriction is put on the kind of carrier, and any of an inorganic oxide carrier, another inorganic carrier and an organic carrier can be used, but the inorganic oxide carrier or the other inorganic carrier is particularly preferable from the viewpoint of morphology control.

Typical examples of the inorganic oxide carrier include $SiO_2$, $Al_2O_3$, MgO, $ZrO_2$, $TiO_2$, $Fe_2O_3$, $B_2O_3$, CaO, ZnO, BaO, $ThO_2$ and mixtures thereof such as silica-alumina, zeolites, ferrites and glass fibers. Above all, $SiO_2$ and $Al_2O_3$ are particularly preferable. The above-mentioned inorganic oxide carrier may contain a small amount of a carbonate, a nitrate, a sulfate or the like.

On the other hand, examples of usable carriers other than mentioned above include magnesium compounds represented by the general formula $MgR^{16}_x X^4_y$ typified by magnesium compounds such as $MgCl_2$ and $Mg(OC_2H_5)_2$, and complexes thereof. In this general formula, $R^{16}$ is an alkyl group having 1 to 20 carbon atoms, an alkoxy group having 1 to 20 carbon atoms or an aryl group having 6 to 20 carbon atoms; $X^4$ is a halogen atom or an alkyl group having 1 to 20 carbon atoms; x is 0 to 2; and y is 0 to 2, and x+y=2. A plurality of $R^{16}$s and $X^4$S may be the same or different.

Examples of the organic carrier include polymers such as polystyrenes, styrene-divinylbenzene copolymers, polyethylenes, polypropylenes, substituted polystyrenes and polyacrylates, starch and carbon.

Preferable examples of the carrier which can be used in the present invention include $MgCl_2$, $MgCl(OC_2H_5)$, $Mg(OC_2H_5)_2$, $SiO_2$ and $Al_2O_3$. The characteristics of the carrier depend upon its kind and preparation method, but the average particle diameter of the carrier is usually in the range of 1 to 300 µm, preferably 10 to 200 µm, more preferably 20 to 100 µm.

If the particle diameter is small, the amount of a fine powder in the polymer increases, and if it is large, the amount of the coarse particles increase in the polymer, which leads to the deterioration of bulk density and the clogging of a hopper.

The specific surface area of the carrier is usually in the range of 1 to 1000 $m^2/g$, preferably 50 to 500 $m^2/g$, and the pore volume of the carrier is usually in the range of 0.1 to 5 $cm^3/g$, preferably 0.3 to 3 $cm^3/g$.

If either of the specific surface area or the pore volume deviates from the above-mentioned range, the catalytic activity deteriorates on occasion. The specific surface area or the pore volume can be determined on the basis of the volume of a nitrogen gas adsorbed, for example, by a BET method [J. Am. Chem. Soc., Vol. 60, p. 309 (1983)].

Furthermore, the carrier is suitably calcined usually at 150° to 1000° C., preferably 200° to 800° C. prior to its use.

In the case that at least one of the catalytic components is supported on the above-mentioned carrier, at least one of the catalytic components (A) and (B), preferably both of the catalytic components (A) and (B) are supported, which is desirable from the viewpoints of morphology control and applicability to a process such as gaseous phase polymerization.

No particular restriction is put on a method for supporting at least one of the catalytic components (A) and (B) on the carrier, but there can be used, for example, (1) a method which comprises mixing at least one of the catalytic components (A) and (B) with the carrier, (2) a method which comprises first treating the carrier with an organic aluminum compound or a halogen-containing silicon compound, and then mixing at least one of the catalytic components (A) and (B) with the treated carrier in an inert solvent, (3) a method which comprises reacting the carrier, one or both of the catalytic components (A) and (B) and an organic aluminum compound or a halogen-containing silicon compound, (4) a method which comprises supporting the component (A) or the component (B) on the carrier, and then mixing the carrier with the component (B) or the component (A), (5) a method which comprises mixing the carrier with a catalytic reaction product of the component (A) and the component (B), or (6) a method which comprises carrying out a catalytic reaction of the component (A) and the component (B) in the presence of the carrier.

In the reaction of the above-mentioned methods (4), (5) and (6), the organic aluminum compound which is the component (C) can be added.

The thus obtained catalyst may be used for the polymerization after it has been taken out as a solid by distilling off a solvent, or it may be used as it is without isolation.

In the present invention, the catalyst can be prepared by carrying out an operation of supporting at least one of the component (A) and the component (B) on the carrier in a polymerization system. For example, a method can be employed which comprises adding at least one of the components (A) and (B), the carrier and if necessary, the organic aluminum compound as the above-mentioned component (C) to the system, further adding an olefin such as ethylene as much as a pressure of from atmospheric pressure to 20 $kg/cm^2$, and then carrying out prepolymerization at −20° to 200° C. for a period of 1 minute to 2 hours to form catalyst particles.

In the present invention, a weight ratio of the compound component (B-1) to the carrier is preferably in the range of 1:5 to 1:10000, more preferably 1:10 to 1:500; a weight ratio of the compound component (B-2) to the carrier is preferably in the range of 1:0.5 to 1:1000, more preferably 1:1 to 1:50; and a weight ratio of the compound component (B-3) to the carrier is preferably in the range of 1:5 to 1:10000, more preferably 1:10 to 1:500. In the case that two or more kinds of catalytic components (B) is used in the form of a mixture, the weight ratios of these components (B) to the carrier are desirably within the above-mentioned ranges, respectively. A weight ratio of the component (A) to the carrier is preferably 1:5 to 1:10000, more preferably 1:10 to 1:500.

If the use ratio of the component (B) [the component (B-1), the component (B-2) or the component (B-3)] to the carrier, or the use ratio of the component (A) to the carrier deviates from the above-mentioned range, the activity deteriorates on occasion. The average particle diameter of the thus prepared catalyst for polymerization according to the present invention is usually in the range of 2 to 200 µm, preferably 10 to 150 µm, more preferably 20 to 100 µm, and the specific surface area of the catalyst is usually in the range of 20 to 1000 $m^2/g$, preferably 50 to 500 $m^2/g$. If the average particle diameter of the catalyst is less than 2 µm, the amount of a fine powder in the polymer increases sometimes, and if it is more than 200 µm, the amount of the coarse particles increase in the polymer sometimes. If the specific surface area of the catalyst is less than 20 $m^2/g$, the activity deteriorates on occasion, and it is more than 1000 $m^2/g$, the bulk density of the polymer deteriorates sometimes. Furthermore, in the catalyst of the present invention, the amount of the transition metal in 100 g of the carrier is usually in the range of 0.05 to 10 g, preferably 0.1 to 2 g. If the amount of the transition metal deviates from the above-mentioned range, the activity deteriorates on occasion.

This technique of supporting the components on the carrier enables the formation of the industrially advantageous polymer having the high bulk density and an excellent particle diameter distribution.

According to the preparation method of the olefin polymer regarding the present invention, the homopolymerization of an olefin or the copolymerization of an olefin and another olefin and/or another monomer (i.e., the copolymerization of different kinds of olefins, the copolymerization of an olefin and another monomer, or the copolymer of different kinds of olefins and another monomer) can be suitably carried out by the use of the above-mentioned catalyst for polymerization.

No particular restriction is put on the kind of olefins, but α-olefins having 2 to 20 carbon atoms are preferable. Examples of the α-olefins include ethylene, propylene, 1-butene, 3-methyl-1-butene, 1-pentene, 1-hexene, 4-methyl-1-pentene, 1-octene, 1-decene, 1-dodecene, 1-tetradecene, 1-hexadecene, 1-octadecene, 1-eicosene, styrene, p-methylstyrene, isopropylstyrene and t-butylstyrene. The above-mentioned other olefin can also suitably be selected from these olefins mentioned above.

In the present invention, the above-mentioned olefins may be used singly or in a combination of two or more thereof. In the case that two or more olefins are copolymerized, these olefins can optionally be combined. At this time, for example, when propylene is copolymerized with ethylene or ethylene is copolymerized with an α-olefin having 3 to 10 carbon atoms, a copolymerization ratio (molar ratio) of propylene and ethylene, or ethylene and the α-olefin having 3 to 10 carbon atoms is usually selected in the range of 99.9:0.1 to 0.1 to 99.9, preferably 99.5:0.5 to 75.0:25.0.

In the present invention, the above-mentioned olefin may be copolymerized with another monomer, and examples of the other monomer which can be used at this time include chain diolefins such as butadiene, isoprene and 1,5-hexadiene, cyclic olefins such as norbornene, 1,4,5,8-dimethanol-1,2,3,4,4a,5,8,8a-octahydronaphthalene and 2-norbornene, cyclic diolefins such as norbornadiene, 5-ethylidenenorbornene, 5-vinylnorbornene and dicyclopentadiene, unsaturated esters such as ethyl acrylate and methyl methacrylate, lactones such as β-propiolactone, β-butyrolactone and γ-butyrolactone, lactams such as ε-caprolactam and δ-valerolactam, and epoxides such as epoxypropane and 1,2-epoxybutane.

Incidentally, the catalyst for polymerization of the present invention can be used not only for the polymerization of the above-mentioned olefin but also for the polymerization of a monomer other than the olefin.

In the present invention, no particular restriction is put on a polymerization method, and any of a slurry polymerization method, a gaseous phase polymerization method, a bulk polymerization method, a solution polymerization method and a suspension polymerization method can be used, but the slurry polymerization method and the gaseous phase polymerization method are preferable from the viewpoints of a high productivity and less process steps.

With regard to the conditions of the polymerization, a polymerization temperature is usually in the range of $-100°$ to $250°$ C., preferably $-50°$ to $200°$ C., more preferably $0°$ to $130°$ C. Furthermore, a use ratio of the catalyst to the reaction material is such that the material monomer/the above-mentioned component (A) (molar ratio) is preferably in the range of 1 to $10^8$, more preferably 100 to $10^5$. Moreover, a polymerization time is usually in the range of 5 minutes to 10 hours, and a reaction pressure is preferably in the range of from atmospheric pressure to 200 kg/cm$^2$G, more preferably from atmospheric pressure to 100 kg/cm$^2$G.

The molecular weight of the polymer can be adjusted by selecting the kinds and the amounts of catalytic components and the polymerization temperature, and by carrying out the polymerization in the presence or absence of hydrogen.

In the case that a polymerization solvent is employed, examples of the usable solvent include aromatic hydrocarbons such as benzene, toluene, xylene and ethylbenzene, alicyclic hydrocarbons such as cyclopentane, cyclohexane and methylcyclohexane, aliphatic hydrocarbons such as pentane, hexane, heptane and octane, and halogenated hydrocarbons such as chloroform and dichloromethane. These solvents may be used singly or in a combination of two or more thereof. In addition, a monomer such as an α-olefin may be used as the solvent. In a certain polymerization method, the polymerization can be carried out in the absence of any solvent.

No particular restriction is put on the molecular weight of the polymer which can be obtained by such a process, but its intrinsic viscosity [η] (measured in decalin at 135° C.) is preferably 0.1 dl/g or more, more preferably 0.2 dl/g or more. If the intrinsic viscosity is less than 0.1 dl/g, sufficient mechanical properties cannot be obtained, and hence the polymer having such a low intrinsic viscosity is not practical.

In the present invention, prepolymerization can be carried out by the use of the above-mentioned catalyst for polymerization. The prepolymerization can be accomplished by bringing a small amount of an olefin into contact with the solid catalytic component, but its procedure is not particularly limited and a known method can be used. No particular restriction is put on the olefin for use in the prepolymerization, and such olefins as mentioned above, for example, ethylene, α-olefins having 3 to 20 carbon atoms and mixtures thereof are usable, but it is advantageous to employ the same olefin as used in the polymerization.

A prepolymerization temperature is usually in the range of $-20°$ to $200°$ C., preferably $-10°$ to $130°$ C., more preferably $0°$ to $80°$ C. In the prepolymerization, an inactive hydrocarbon, an aliphatic hydrocarbon, an aromatic hydrocarbon or a monomer can be used as the solvent. Above all, the aliphatic hydrocarbon is particularly preferable. The prepolymerization may be carried out in the absence of any solvent.

In the prepolymerization, conditions are desirably regulated so that the intrinsic viscosity [η] (measured in decalin at 135° C.) of a prepolymerized product may be 0.2 dl/g or more, preferably 0.5 dl/g or more and so that the amount of the prepolymerized product per mmol of the transition metal component in the catalyst may be in the range of 1 to 10,000 g, preferably 10 to 1,000 g.

Thus, an olefin polymer of the present invention having a uniform composition and a narrow molecular weight distribution can efficiently be obtained.

Next, the present invention will be described in more detail with reference to examples, but the scope of the present invention should not be limited at all by these examples.

REFERENCE PROPARATION EXAMPLE 1

Preparation of (1,1'-dimethylsilylene)(2,2'-dimethylsilylene)-bis(cyclo-pentadienyl)zirconium dichloride (A-2)

2.4 g (9.6 mmol) of (1,1'-dimethylsilylene)(2,2'-dimethylsilylene)-bis(cyclopentadiene) was dissolved in 50 ml of hexane, and 19.2 mmol of n-butyllithium (a hexane solution containing n-butyllithium of 1.5 mol per liter of hexane) was added dropwise at $-78°$ C. to the solution, followed by stirring at room temperature for 5 hours. Next, the solvent was distilled off, and the resultant residue was washed once with 20 ml of hexane, and then dried to obtain a white solid. Afterward, this solid was suspended in 50 ml of toluene, and 2.3 g (9.6 mmol) of zirconium tetrachloride was added at $-20°$ C. to the suspension. After stirring for 12 hours at room temperature, the solvent was distilled off, and recrystallization was then carried out from dichloromethane-hexane to obtain 1.1 g of (1,1'-dimethylsilylene)(2,2'-dimethylsilylene)-bis(cyclopenta-dienyl)zirconium dichloride in the state of a colorless crystal.

The $^1$H-NMR of this product was measured, and the following results were obtained.

$^1$H-NMR (90 MHz, CDCl$_3$): δ 0.57 [6H, s, (CH$_3$)$_2$Si], 0.93 [6H, s, (CH$_3$)$_2$Si], 6.47 (2H, t, —CH—), 6.98 (4H, d, —CH—).

Incidentally, (1,1'-dimethylsilylene)(2,2'-dimethylsilylene)-bis(cyclopentadiene) was synthesized in accordance with a procedure described in "Organometallics", Vol. 10, p. 1787 (1991).

EXAMPLE 1

Preparation of (1,1'-dimethylsilylene)-(2,2'-isopropylidene)-bis(cyclopentadienyl)zirconium dichloride (A-1)

0.7 g (3.2 mmol) of (1,1'-dimethylsilylene)(2,2'-isopropylidene)-bis(cyclopentadiene) was dissolved in 30 ml of hexane, and 6.48 mmol of n-butyllithium (a hexane solution containing n-butyllithium of 1.5 mol per liter of hexane) was added dropwise at $-78°$ C. to the solution, followed by stirring at room temperature for 5 hours. Next, the solvent was distilled off, and the resultant residue was washed with 20 ml of hexane, and the washed white solid was then dried under reduced pressure. Afterward, to the toluene suspension (20 ml) of this solid, 0.8 g (3.2 mmol) of zirconium tetrachloride was added, and after stirring for 12 hours at room temperature, the solvent was distilled off. Next, recrystallization was carried out from dichloromethane-hexane to obtain 0.3 g of (1,1'-dimethylsilylene)-(2,2'-isopropylidene)-bis (cyclopentadienyl)zirconium dichloride in the state of a light yellow powder.

The $^1$H-NMR of this product was measured, and the following results were obtained.

$^1$H-NMR (90 MHz, CDCl$_3$): δ 1.01 [3H, s, (C$\underline{H}_3$)$_2$Si], 0.54 [3H, s, (C$\underline{H}_3$)$_2$Si], 1.52 [3H, s, (C$\underline{H}_3$)$_2$C], 2.16 [3H, s, (C$\underline{H}_3$)$_2$C], 6.17 (2H, m, —CH—), 6.53 (2H, m, —CH—), 6.82 (2H, m, —CH—).

Incidentally, (1,1'-dimethylsilylene)( 2,2'-isopropylidene)-bis(cyclopentadiene) was synthesized in accordance with a procedure described in "Organometallics", Vol. 10, p. 3739 (1991).

EXAMPLE 2

In a 1-liter autoclave heated and dried under reduced pressure were placed 360 ml of toluene, 40 ml of 1-octene and 1 mmol of triisobutylaluminum (TIBA) at room temperature under a nitrogen atmosphere, and the temperature of the solution was then raised up to 60° C. with stirring. Afterward, 1 μmol of (1,1'-dimethylsilylene)(2,2'-isopropylidene)-bis(cyclopentadienyl)zirconium dichloride obtained in Example 1 and 1 μmol of N,N'-dimethylanilinium tetrakis(pentafluorophenyl)borate were placed in the autoclave at 60° C., and the mixture was then heated up to 80° C. Next, while ethylene was continuously introduced into the autoclave at 80° C. so as to maintain 8 atm, polymerization was carried out for 1 hour.

After the completion of the reaction, the resultant reaction product was poured into a methanol-hydrochloric acid solution, and then sufficiently stirred, followed by filtration. Next, the collected product was sufficiently washed with methanol, and then dried to obtain a polymer. The yield and characteristics of the obtained polymer were measured, and the obtained results are shown in Table 1.

EXAMPLE 3

The same procedure as in Example 2 was repeated except that 1 mmol of TIBA was replaced with 6 mmol of methylaluminoxane and N,N'-dimethylanilinium tetrakis-(pentafluorophenyl)borate was not used. The results are shown in Table 1.

EXAMPLE 4

The same procedure as in Example 2 was repeated except that 40 ml of 1-octene was not used and a reaction time was set to 30 minutes. The results are shown in Table 1.

EXAMPLE 5

The same procedure as in Example 3 was repeated except that 40 ml of 1-octene was not used and a reaction time was set to 30 minutes. The results are shown in Table 1.

Reference Example 1

The same procedure as in Example 2 was repeated except that (1,1'-dimethylsilylene)(2,2'-isopropylidene)-bis (cyclopentadienyl)zirconium dichloride was replaced with (1,1'-dimethylsilylene)(2,2'-dimethylsilylene)-bis(cyclopentadienyl)zirconium dichloride obtained in Reference Preparation Example 1. The results are shown in Table 1.

Reference Example 2

The same procedure as in Example 3 was repeated except that (1,1'-dimethylsilylene)(2,2'-isopropylidene)-bis (cyclopentadienyl)zirconium dichloride was replaced with (1,1'-dimethylsilylene)(2,2'-dimethylsilylene)-bis(cyclopentadienyl)zirconium dichloride obtained in Reference Preparation Example 1. The results are shown in Table 1.

Reference Example 3

The same procedure as in Example 4 was repeated except that (1,1'-dimethylsilylene)(2,2'-isopropylidene)-bis (cyclopentadienyl)zirconium dichloride was replaced with (1,1'-dimethylsilylene)(2,2'-dimethylsilylene)-bis(cyclopentadienyl)zirconium dichloride obtained in Reference Preparation Example 1. The results are shown in Table 1.

Reference Example 4

The same procedure as in Example 5 was repeated except that (1,1'-dimethylsilylene)(2,2'-isopropylidene)-bis (cyclopentadienyl)zirconium dichloride was replaced with (1,1'-dimethylsilylene)(2,2'-dimethylsilylene)-bis(cyclopentadienyl)zirconium dichloride obtained in Reference Preparation Example 1. The results are shown in Table 1.

TABLE 1-1

| | Catalyst | | Polymer | |
|---|---|---|---|---|
| | Main Catalyst | Cocatalyst | Kind | Yield (g) |
| Example 2 | A-1 | TIBA B-1 | Ethylene-1-octene Copolymer | 45.7 |
| Example 3 | A-1 | MAO | Ethylene-1-octene Copolymer | 35.1 |
| Example 4 | A-1 | TIBA B-1 | Polyethylene | 37.4 |
| Example 5 | A-1 | MAO | Polyethylene | 30.9 |
| Ref. Ex. 1 | A-2 | TIBA B-1 | Ethylene-1-octene Copolymer | 29.5 |
| Ref. Ex. 2 | A-2 | MAO | Ethylene-1-octene Copolymer | 27.3 |
| Ref. Ex. 3 | A-2 | TIBA B-1 | Polyethylene | 35.0 |
| Ref. Ex. 4 | A-2 | MAO | Polyethylene | 25.6 |

TABLE 1-2

| | Polymer | | | |
|---|---|---|---|---|
| | Intrinsic* Viscosity [η] (dl/g) | Melting point** (°C.) | 1-octene Unit Content (mol %) | Melting Energy** ΔH (J/q) |
| Example 2 | 0.92 | 108.7 | 5.8 | 22 |
| Example 3 | 0.49 | 109.8 | 7.3 | 13 |
| Example 4 | 2.37 | 133.5 | — | 200 |
| Example 5 | 1.87 | 135.8 | — | 257 |
| Ref. Ex. 1 | 0.80 | 115.6 | 4.0 | 92 |
| Ref. Ex. 2 | 0.87 | 115.5 | 3.9 | 58 |

TABLE 1-2-continued

|  | Polymer | | | |
|---|---|---|---|---|
|  | Intrinsic* Viscosity [η] (dl/g) | Melting point** (°C.) | 1-octene Unit Content (mol %) | Melting Energy** ΔH (J/q) |
| Ref. Ex. 3 | 2.82 | 135.0 | — | 200 |
| Ref. Ex. 4 | 3.51 | 133.5 | — | 200 |

*The intrinsic viscosity was measured in decalin at 135° C.
**The melting point was determined on the basis of the results of second heat at a heating rate of 10° C./min by the use of DSC.

As understood from Table 1, in the case that (1,1'-dimethylsilylene)(2,2'-isopropylidene)-bis(cyclopentadienyl)zirconium dichloride is used as a main catalytic component, the copolymerizability of ethylene-1-octene copolymerization is better than in the case that (1,1'-dimethylsilylene)(2,2'-dimethylsilylene)-bis(cyclopentadienyl)zirconium dichloride is used.

EXAMPLE 6
Preparation of (1,1'-dimethylsilylene)-(2,2'-isopropylidene)-bis(cyclopentadienyl)titanium dichloride (A-3)

2.3 g (10 mmol) of (1,1'-dimethylsilylene)(2,2'-isopropylidene)-bis(cyclopentadiene) was dissolved in 100 ml of hexane, and 20 mmol of n-butyllithium was added dropwise at −78° C. to the solution, followed by stirring at room temperature for 12 hours. Next, the solvent was distilled off, and the resultant residue was washed with 50 ml of hexane, and then dried under reduced pressure to obtain a white solid. Afterward, this solid was suspended in 50 ml of tetrahydrofuran, and a tetrahydrofuran solution containing 3.7 g (10 mmol) of a titanium trichloride-three tetrahydrofuran complex was added at −78° C. to the suspension. Next, the temperature of the solution was gradually returned to room temperature, followed by stirring for 12 hours. Afterward, 4.3 g (30 mmol) of silver chloride was added to this suspension, and the mixture was then stirred at room temperature for 2 days. The solvent was distilled off, and recrystallization was then carried out from ether to obtain 0.2 g of (1,1'-dimethylsilylene)( 2,2'-isopropylidene)-bis(cyclopentadienyl)titanium dichloride in the state of a red powder.

The $^1$H-NMR of this product was measured, and the following results were obtained.

$^1$H-NMR (90 MHz, CDCl$_3$): δ 0.43 [3H, s, (CH$_3$)$_2$Si], 1.02 [3H, s, (CH3)$_2$Si], 1.36 (3H, S, (CH$_3$)$_2$C), 2.18 (3H, S, (CH$_3$)$_2$C), 6.3–7.1 (6H, m, —CH—).

In addition, some peaks attributed to impurities were slightly observed.

EXAMPLE 7

In a 1-liter autoclave heated and dried under reduced pressure were placed 360 ml of toluene, 40 ml of 1-octene and 1 mmol of triisobutylaluminum (TIBA) at room temperature under a nitrogen atmosphere, and the temperature of the solution was then raised up to 60° C. with stirring. Afterward, 1 μmol of (1,1'-dimethylsilylene)(2,2'-isopropylidene)-bis(cyclopentadienyl)titanium dichloride obtained in Example 6 and 1 μmol of N,N'-dimethylanilinium tetrakis(pentafluorophenyl)borate were placed in the autoclave at 60° C., and the mixture was then heated up to 80° C. Next, while ethylene was continuously introduced into the autoclave at 80° C. so as to maintain 8 atm, polymerization was carried out for 1 hour.

After the completion of the reaction, the resultant reaction product was poured into a methanol-hydrochloric acid solution, and then sufficiently stirred, followed by filtration. Next, the collected product was sufficiently washed with methanol, and then dried to obtain a polymer. The results are shown in Table 2.

EXAMPLE 8

The same procedure as in Example 7 was repeated except that 1 mmol of TIBA was replaced with 6 mmol of methylaluminoxane and N,N'-dimethylanilinium tetrakis (pentafluorophenyl)borate was not used. The results are shown in Table 2.

EXAMPLE 9

The same procedure as in Example 7 was repeated except that 40 ml of 1-octene was not used. The results are shown in Table 2.

EXAMPLE 10

The same procedure as in Example 8 was repeated except that 40 ml of 1-octene was not used. The results are shown in Table 2.

TABLE 2-1

|  | Catalyst | | Polymer | |
|---|---|---|---|---|
|  | Main Catalyst | Cocatalyst | Kind | Yield (g) |
| Example 7 | A-3 | TIBA B-1 | Ethylene-1-octene Copolymer | 0.85 |
| Example 8 | A-3 | MAO | Ethylene-1-octene Copolymer | 1.90 |
| Example 9 | A-3 | TIBA B-1 | Polyethylene | 12.7 |
| Example 10 | A-3 | MAO | Polyethylene | 8.90 |

A-3: (1,1'-dimethylsilylene)(2,2'-isopropylidene)-bis(cyclopentadienyl) titanium chloride

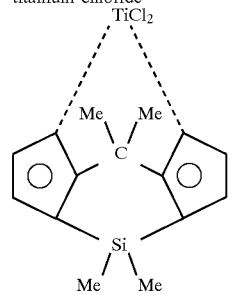

TABLE 2-2

|  | Polymer | | | | |
|---|---|---|---|---|---|
|  | Intrinsic* Viscosity [η] (dl/g) | Melting Point** (°C.) | 1-octene Unit Content (mol %) | Catalytic Activity (kg/g Tihr) | Melting Energy** ΔH (J/g) |
| Example 7 | 2.00 | None | 10.4 | 18 | 10.0 |
| Example 8 | 2.96 | None | 9.8 | 40 | 11.3 |
| Example 9 | 7.38 | 135 | — | 265 | 144 |

TABLE 2-2-continued

|  | Polymer | | | | |
|---|---|---|---|---|---|
|  | Intrinsic* Viscosity [η] (dl/g) | Melting Point** (°C.) | 1-octene Unit Content (mol %) | Catalytic Activity (kg/g Tihr) | Melting Energy** ΔH (J/g) |
| Example 10 | — | 134 | — | 186 | 126 |

*The intrinsic viscosity was measured in decalin at 135° C.
**The melting point was determined on the basis of the results of second heat at a heating rate of 10° C./min by the use of DSC.

EXAMPLE 11

Preparation of (1,1'-dimethylsilylene)-(2,2'-isopropylidene)-bis(cyclopentadienyl)titanium dichloride (A-4)

5.57 g (24.2 mmol) of (1,1'-dimethylsilylene)(2,2'-isopropylidene)-bis(cyclopentadiene) was dissolved in 100 ml of THF (tetrahydrofuran), and 48.8 nmnol of n-butyllithium was added dropwise at −78° C. to the solution, followed by stirring at room temperature for 8 hours. Next, the solvent was distilled off, and the resultant residue was washed with 100 ml of hexane and next 100 ml of THF, and then dried under reduced pressure to obtain 1.00 g (4.16 mmol) of a white solid of a lithium salt. Afterward, this solid was suspended in 50 ml of tetrahydrofuran, and a tetrahydrofuran solution (60 ml) containing 1.54 g (4.16 mmol) of a titanium trichloride-three tetrahydrofuran complex was added at room temperature to the suspension, followed by stirring for 12 hours. Next, 11.08 g (77 mmol) of silver chloride was added to this suspension, and the mixture was then stirred at room temperature for 3 hours. The solvent was distilled off, and extraction with ether, the removal of ether by distillation and washing with hexane were done in turn to obtain 35 mg of (1,1'-dimethylsilylene) (2,2'-isopropylidene)-bis(cyclopentadienyl)-titanium dichloride in the state of a red powder.

The $^1$H-NMR of this product was measured, and the following results were obtained.

$^1$H-NMR (90 MHz, CDCl$_3$): δ 0.43 [3H, s, (C$\underline{H}_3$)$_2$Si], 1.02 [3H, s, (C$\underline{H}_3$)$_2$Si], 1.36 (3H, s, (C$\underline{H}_3$)$_2$C), 2.18 (3H, s, (C$\underline{H}_3$)$_2$C), 6.3–7.1 (6H, m, —CH—).

EXAMPLE 12

In a 1-liter autoclave heated and dried under reduced pressure were placed 360 ml of toluene, 40 ml of 1-octene and 1 mmol of triisobutylaluminum (TIBA) at room temperature under a nitrogen atmosphere, and the temperature of the solution was then raised up to 60° C. with stirring. Afterward, 1 μmol of (1,1'-dimethylsilylene)(2,2'-isopropylidene)-bis(cyclopentadienyl)titanium dichloride obtained in Example 11 and 1 μmol of N,N'-dimethylanilinium tetrakis(pentafluorophenyl)borate were placed in the autoclave at 60° C., and the mixture was then heated up to 80° C. Next, while ethylene was continuously introduced into the autoclave at 80° C. so as to maintain 8 atm, polymerization was carried out for 1 hour.

After the completion of the reaction, the resultant reaction product was poured into a methanol-hydrochloric acid solution, and then sufficiently stirred, followed by filtration. Next, the collected product was sufficiently washed with methanol, and then dried to obtain a polymer.

The results are shown in Table 3.

EXAMPLE 13

The same procedure as in Example 12 was repeated except that 1 mmol of TIBA was replaced with 6 mmol of methylaluminoxane and N,N'-dimethylanilinium tetrakis (pentafluorophenyl)borate was not used. The results are shown in Table 3.

EXAMPLE 14

The same procedure as in Example 13 was repeated except that 3 μmol of (1,1'-dimethylsilylene)(2,2'-isopropylidene)-bis(cyclopentadienyl)titanium dichloride and 3 mmol of methylaluminoxane were used and 560 ml of toluene was used. The results are shown in Table 3.

EXAMPLE 15

The same procedure as in Example 14 was repeated except that 20 ml of 1-octene and 580 ml of toluene were used. The results are shown in Table 3.

TABLE 3-1

|  | Main Catalyst | | Cocatalyst | |
|---|---|---|---|---|
|  | Kind | Amount (μmol) | Kind | Amount (μmol) |
| Example 12 | A-4 | 1 | TIBA | 1 |
|  |  |  | B-1 | 1 × 10$^{-3}$ |
| Example 13 | A-4 | 1 | MAO | 6 |
| Example 14 | A-4 | 3 | MAO | 3 |
| Example 15 | A-4 | 3 | MAO | 3 |

TABLE 3-2

|  | Ethylene (atm) | 1-octene (ml) | Temp. (°C.) | Time (min) |
|---|---|---|---|---|
| Example 12 | 8 | 40 | 80 | 60 |
| Example 13 | 8 | 40 | 80 | 60 |
| Example 14 | 8 | 40 | 80 | 60 |
| Example 15 | 8 | 20 | 80 | 60 |

A-4: (1,1'-dimethylsilylene)(2,2'-isopropylidene)-bis(cyclopentadienyl) titanium dichloride (which is the same as the above-mentioned A-3)

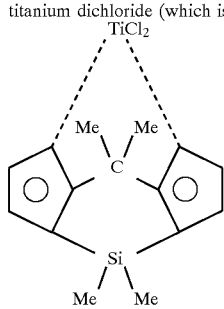

TABLE 3-3

|  | Polymer | | | |
|---|---|---|---|---|
|  | Yield (g) | Intrinsic Viscosity [η] (dl/g) | 1-octene Unit Content (mol %) | Melting Point*$^1$ (Tm) (°C.) |
| Example 12 | 4.3 | 0.90 | 9.2 | 67.3 |
| Example 13 | 9.6 | 2.28 | 9.1 | 59.7 |
| Example 14 | 39.6 | 3.85 | 5.1 | 85.2 |
| Example 15 | 39.3 | 5.90 | 3.1 | 100.6 |

TABLE 3-4

| | Polymer | | | |
|---|---|---|---|---|
| | Melting Energy ΔH (J/g) | MW*2 | Mn*3 | Q*4 |
| Example 12 | 45.2 | 39600 | 18000 | 2.2 |
| Example 13 | 52.5 | 144000 | 66600 | 2.2 |
| Example 14 | 43.9 | 223000 | 107000 | 2.1 |
| Example 15 | 83.1 | 208000 | 101000 | 2.1 |

*1: Melting point (Tm): The melting point was determined on the basis of the results of second heat at a heating rate of 10° C./min by the use of DSC, and in the case that it was 80° C. or less, it represented a temperature at a broad peak.
*2: Mw: Weight-average molecular weight
*3: Mn: Number-average molecular weight
*4: Q = Mw/Mn

EXAMPLE 16

Preparation of (1,1'-dimethylsilylene)(2,2'-isopropylidene)-bis(indenyl)zirconium dichloride (A-5)

(1) In a 1-liter three-necked flask purged with nitrogen were placed 10.8 g of magnesium and 45 ml of THF, and 0.6 ml of dibromomethane was then added dropwise thereto. After stirring for 5 minutes, the solvent was distilled off under reduced pressure, and 200 ml of THF was further added. Next, a solution obtained by dissolving 18.3 g (0.105 mol) of α,α'-dichloro-o-xylene in 300 ml of THF was added dropwise to the flask at room temperature over 3 hours. After the completion of the dropping, the solution was further stirred for 15 hours and then cooled to −78° C., and a THF (100 ml) solution containing 6.8 g (36.2 mmol) of diethyl dimethylmalonate was added dropwise over 1 hour. Afterward, the temperature of the solution was returned to room temperature, and after stirring for 2 hours, 100 ml of water was added at room temperature. The mixture was filtered with suction, and the solvent was then distilled off under reduced pressure. Next, extraction was made with dichloromethane and a 1N aqueous ammonium chloride solution, and the resultant organic layer was washed twice with water and then dried over magnesium sulfate. A solid was removed by filtration, and the solvent was then distilled off, thereby obtaining a yellow oil. Furthermore, the oil was purified through column chromatography using active alumina and then recrystallized from hexane to obtain 4.8 g (15.9 mmol, yield: 44%) of a desired compound (hereinafter referred to as "Compound a") in the state of a colorless crystal.

The $^1$H-NMR of this product was measured, and the following results were obtained.

$^1$H-NMR (CDCl$_3$): δ 1.235 (s, 6H, CH$_3$), 3.002 (d, J=16.4 Hz) and 3.470 (d, J=16.4 Hz) (8H, CH$_3$), 3.767 (s, 2H, OH), 7.2–7.4 (mul, 8H, PhH)

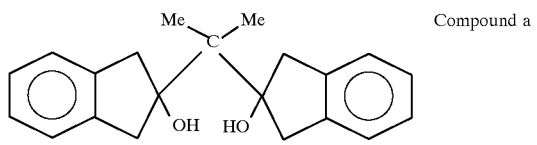

Compound a wherein Me is a methyl group, and the same shall apply hereinafter.

(2) 4.8 g (15.9 mmol) of Compound a obtained in the paragraph (1) was dissolved in 30 ml of dichloromethane, and 3.04 g (15.9 mmol) of p-toluenesulfonic acid was added, followed by reflux for 8 hours. The resultant reaction mixture was washed with sodium hydrogencarbonate and water, and then dried over magnesium sulfate. A precipitate was removed by filtration, and the solvent was then distilled off, thereby obtaining a yellow oil. Furthermore, this oil was purified through column chromatography using silica gel and then recrystallized from hexane to obtain 2.3 g (8.6 mmol, yield: 54%) of a desired compound (hereinafter referred to as "Compound b") in the state of a colorless crystal.

The $^1$H-NMR of this product was measured, and the following results were obtained.

$^1$H-NMR (CDCl$_3$): δ 1.586 (s, 6H, CH$_3$), 3.470 (s, 4H, CH$_2$), 3.767 (s, 2H, CpH), 6.9–7.5 (mul, 8H, PhH)

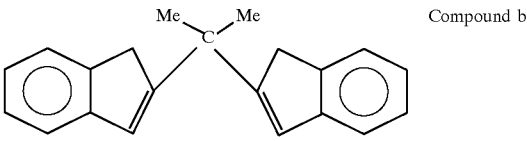

Compound b (3) In a Schlenk tube purged with nitrogen were placed 6.2 g (22.7 mmol) of the Compound b obtained by repeating the reactions of the above-mentioned (1) and (2) and 50 ml of diethyl ether. Next, the solution was cooled to −78° C., and 28.4 ml (45.4 mmol) of an n-butyllithium solution having a concentration of 1.6 mol/liter was added dropwise thereto. The temperature of the solution was returned to room temperature, and at this time, a white precipitate was gradually deposited. After stirring at room temperature for 3 hours, the supernatant liquid was drawn out, and the precipitate was washed twice with a small amount of diethyl ether. Next, the precipitate was dried under reduced pressure to obtain a dilithium salt (hereinafter referred to as "Compound c") in the state of a colorless powder:

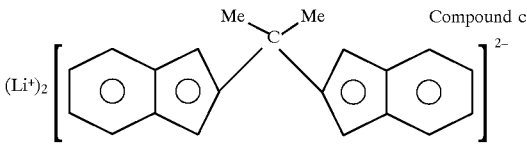

Compound c (4) The dilithium salt (Compound c) obtained above was dissolved in 100 ml of THF. Next, 3.0 g (22.7 mmol) of distilled dichlorodimethylsilane was slowly added dropwise, followed by stirring for 3 hours. The solvent was distilled off, and extraction was then carried out with dichloromethane and water. The resultant organic layer was washed twice with water, and then dehydrated over magnesium sulfate. Afterward, a precipitate was removed by filtration, and recrystallization was then carried out from hexane to obtain 6.5 g (19.6 mmol, yield: 86.5%) of a colorless crystal (the following Compound d).

The $^1$H-NMR of this product was measured, and the following results were obtained.

$^1$H-NMR (CDCl$_3$): δ −0.354 (s, 6H, SiCH$_3$), 1.608 (s, 6H, CCH$_3$), 3.347 (s, 2H, SiCH), 6.785 (s, 2H, CpH), 6.9–7.6 (mul, 8H, PhH)

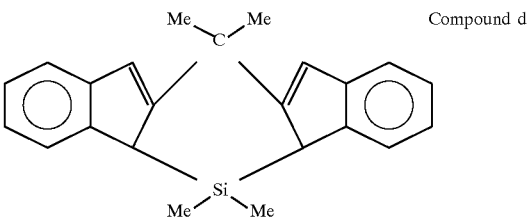

Compound d (5) In a Schlenk tube purged with nitrogen were placed 0.9 g (2.7 mmol) of the Compound b obtained in the above-mentioned (4) and 50 ml of hexane. Next, the solution was cooled to 0° C., and 3.4 ml (5.4 mmol) of an n-butyllithium solution having a concentration of 1.6 mol/liter was added dropwise thereto. The temperature of the solution was returned to room temperature, and at this time, a white precipitate was deposited. After stirring at room temperature for 3 hours, the supernatant liquid was drawn out, and the precipitate was washed twice with hexane. Next, the precipitate was dried under reduced pressure to obtain a dilithium salt (hereinafter referred to as "Compound e") in the state of a pink powder:

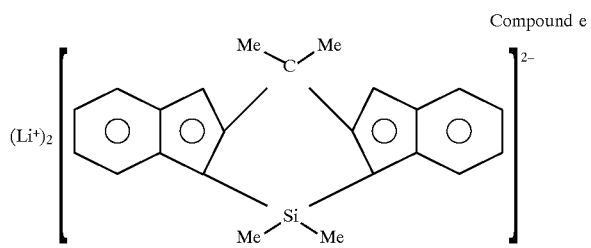

Compound e (6) Toluene was added to the dilithium salt (Compound e) obtained in the above-mentioned (5) to form a suspension. Next, to this suspension, a toluene suspension containing 630 mg (2.7 mmol) of tetrachlorozirconium was added dropwise at 0° C. The temperature of the mixture was returned to room temperature, and after stirring for 24 hours, a precipitate was removed by filtration and the solution was then concentrated. Afterward, recrystallization was done from toluene-hexane to obtain 240 mg (0.508 mmol, yield: 19%) in the state of a yellowish orange crystal (A-5).

The $^1$H-NMR of this product was measured, and the following results were obtained.

$^1$H-NMR (heavy THF): δ −0.172 (s, 3H, SiCH$_3$), 0.749 (s, 3H, SiCH$_3$), 1.346 (s, 3H, CCH$_3$), 2.141 (s, 3H, CCH$_3$), 3.654 (s, 2H, CpH), 6.692 (s, 2H, CpH), 6.9–8.1 (mul, 8H, PhH)

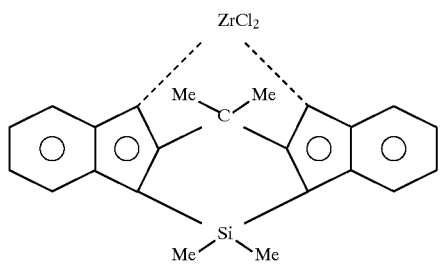

A-5

EXAMPLE 17

In a 1-liter autoclave heated and dried under reduced pressure were placed 360 ml of toluene, 40 ml of 1-octene and 1 mmol of triisobutylaluminum (TIBA) at room temperature under a nitrogen atmosphere, and the temperature of the solution was then raised up to 60° C. with stirring. Afterward, 1 μmol of a zirconium-containing transition metal complex (A-5) obtained in Example 16 and 1 μmol of N,N'-dimethylanilinium tetrakis (pentafluorophenyl)borate were placed in the autoclave at 60° C., and the mixture was then heated up to 80° C. Next, while ethylene was continuously introduced into the autoclave at 80° C. so as to maintain 8 atm, polymerization was carried out for 10 minutes.

After the completion of the reaction, the resultant reaction product was poured into a methanol-hydrochloric acid solution, and then sufficiently stirred, followed by filtration. Next, the collected product was sufficiently washed with methanol, and then dried to obtain a polymer. The results are shown in Table 4.

EXAMPLE 18

The same procedure as in Example 17 was repeated except that 1 mmol of TIBA was replaced with 6 mmol of methylaluminoxane and N,N'-dimethylailinium tetrakis (pentafluorophenyl)borate was not used. The results are shown in Table 4.

EXAMPLES 19 and 20

Examples 19 and 20 were carried out in accordance with the same procedure as in Example 17 except that the amounts of components, reaction temperatures and times were set as shown in Table 4. The results are shown in Table 4.

TABLE 4-1

|  | Main Catalyst | | Cocatalyst | |
| --- | --- | --- | --- | --- |
|  | Kind | Amount (μmol) | Kind | Amount (μmol) |
| Example 17 | A-5 | 1 | TIBA | 1 |
|  |  |  | B-1 | 1 × 10$^{-3}$ |
| Example 18 | A-5 | 1 | MAO | 6 |
| Example 19 | A-5 | 0.5 | TIBA | 1 |
|  |  |  | B-1 | 5 × 10$^{-4}$ |
| Example 20 | A-5 | 0.5 | TIBA | 1 |
|  |  |  | B-1 | 5 × 10$^{-4}$ |

A-5: The zirconium-containing transition metal complex of Example 16

TABLE 4-2

|  | Ethylene (atm) | 1-octene (ml) | Temp. (°C.) | Time (min) |
| --- | --- | --- | --- | --- |
| Example 17 | 8 | 40 | 80 | 10 |
| Example 18 | 8 | 40 | 80 | 10 |
| Example 19 | 9 | 40 | 50 | 60 |
| Example 20 | 9 | 40 | 30 | 60 |

TABLE 4-3

|  | Polymer | | | |
| --- | --- | --- | --- | --- |
|  | Yield (g) | Intrinsic Viscosity [η] (dl/g) | 1-octene Unit Content (mol %) | Melting Point[1] (Tm) (°C.) |
| Example 17 | 110.0 | 0.20 | 4.8 | 103 |
| Example 18 | 38.4 | 0.31 | 4.6 | 104 |
| Example 19 | 73.9 | 0.28 | 4.6 | 104 |
| Example 20 | 16.5 | 0.37 | 6.1 | 94 |

TABLE 4-4

|  | Polymer | | | |
| --- | --- | --- | --- | --- |
|  | Melting Energy ΔH (J/g) | MW[2] | Mn[3] | Q[4] |
| Example 17 | 98.5 | 6900 | 2500 | 2.8 |
| Example 18 | 108.9 | 10000 | 3200 | 3.14 |

TABLE 4-4-continued

|  | Polymer | | | |
|---|---|---|---|---|
|  | Melting Energy ΔH (J/g) | MW*2 | Mn*3 | Q*4 |
| Example 19 | 82.1 | 8100 | 3400 | 2.4 |
| Example 20 | 56.4 | 4600 | 1100 | 4.3 |

*1: Melting point (Tm): The melting point was determined on the basis of the results of second heat at a heating rate of 10° C./min by the use of DSC.
*2: Mw: Weight-average molecular weight
*3: Mn: Number-average molecular weight
*4: Q = Mw/Mn

EXAMPLE 21

In a 1-liter autoclave heated and dried under reduced pressure were placed 400 ml of toluene and 6 mmol of methylaluminoxane at room temperature under a nitrogen atmosphere, and the temperature of the solution was then raised up to 80° C. with stirring. Afterward, 20 mmol of (1,1'-dimethylsilylene)(2,2'-isopropylidene)-bis(cyclopentadienyl)zirconium dichloride obtained in Example 1 was added thereto. Next, while propylene was continuously introduced into the autoclave so as to maintain 3 atm, polymerization was carried out for 1 hour. After the completion of the reaction, the resultant reaction product was poured into a methanol-hydrochloric acid solution and then sufficiently stirred, and the solvent was distilled off. Next, the product was dried to obtain 26.2 g of an atactic polymer.

Reference Example 5

The same procedure as in Example 21 was repeated except that (1,1'-dimethylsilylene)(2,2'-isopropylidene)-bis(cyclopentadienyl)zirconium dichloride was replaced with (1,1'-dimethylsilylene)(2,2'-dimethylsilylene)-bis(cyclopentadienyl)zirconium dichloride obtained in Reference Preparation Example 1. As a result, 11.3 g of an atactic polymer was obtained.

EXAMPLE 22

In a 1-liter autoclave heated and dried under reduced pressure were placed 480 ml of toluene under an argon atmosphere, and its temperature was then raised up to 150° C. Next, argon was introduced thereinto until 11 kg/cm$^2$G had been reached, and ethylene was then introduced so as to attain a total pressure of 24 kg/cm$^2$G might. Afterward, 20 ml of toluene, 6 mmol of methylaluminoxane and 5 μm of a zirconium complex (A-5) obtained in Example 16 which had previously been prepared in a feed pipe were fed to the autoclave, and ethylene was then continuously introduced for 5 minutes so that a total pressure might be 35 kg/cm$^2$G, whereby polymerization was carried out. The results are shown in Table 5.

EXAMPLE 23

The same procedure as in Example 22 was repeated except that toluene was replaced with hexane. The results are shown in Table 5.

EXAMPLE 24

The same procedure as in Example 22 was repeated except that 480 ml of toluene which was a solvent was replaced with 420 ml of hexane and 60 ml of 1-octene, and 1 μmol of a zirconium complex (A-5) was used. The results are shown in Table 5.

EXAMPLE 25

The same procedure as in Example 24 was repeated except that a polymerization temperature was changed to 170° C. The results are shown in Table 5.

TABLE 5-1

|  | Catalyst (μmol) | Methyl-aluminoxane (μmol) | 1-octene (ml) | Total Pressure (kg/cm$^3$G) | Temp. (°C.) |
|---|---|---|---|---|---|
| Example 22 | 5 | 6 | 0 | 35 | 150 |
| Example 23 | 5 | 6 | 0 | 35 | 150 |
| Example 24 | 1 | 6 | 60 | 35 | 150 |
| Example 25 | 1 | 6 | 60 | 35 | 170 |

TABLE 5-2

|  |  |  | Polymer | | |
|---|---|---|---|---|---|
|  | Time (min) | Yield (g) | Melting Point*1 (°C.) | Mw*2 | Q*4 |
| Example 22 | 5 | 97 | 124 | 5700 | 2.7 |
| Example 23 | 5 | 91 | 124 | 5400 | 2.6 |
| Example 24 | 5 | 28 | 121 | 5800 | 2.3 |
| Example 25 | 5 | 3 | 117 | 5600 | 2.4 |

*1Melting point (Tm): The melting point was determined on the basis of the results of second heat at a heating rate of 10° C./min by the use of DSC.
*2Mw: Weight-average molecular weight
*3Q = Mw/Mn (weight-average molecular weight)

Conditions for the measurement of the molecular weight and the molecular weight distribution were as follows.

Device: Waters ALC/GPC 150C
Column: Toso Co., Ltd., TSK HM+GMH6×2
Solvent: 1,2,4-trichlorobenzene
Temperature: 135° C.
Flow rate: This was measured in terms of polyethylene under conditions of 1 ml/min by a GPC method.

EXAMPLE 26

(1) Preparation of (1,1'-dimethylsilylene)(2,2'-isopropylidene)-4,4'-bis(trimethyltin)-bis(cyclopentadiene) (Compound f)

In a 300-ml Schlenk tube purged with nitrogen was placed 8.55 g (37.4 mmol) of (1,1'-dimethylsilylene)(2,2'-isopropylidene)-bis(cyclopentadiene) (Compound g), and 150 ml of degassed and dried diethyl ether was further added thereto. Next, the solution was cooled to −78° C. on a dry ice-methanol bath. To this cooled solution, 45.9 ml (74.8 mmol) of a hexane solution containing 1.63 mol of n-butyllithium per liter of hexane was added dropwise under a nitrogen gas stream with stirring, and the solution was further stirred at room temperature for 12 hours, followed by filtration. The resultant residue was washed with 100 ml of degassed and dried hexane, and they dried under reduced pressure to obtain a dilithium salt.

Next, 8.90 g (37.0 mmol) of this dilithium salt was suspended in 150 ml of degassed and dried tetrahydrofuran, and the suspension was then cooled to −78° C. on a dry ice-methanol bath. While the cooled suspension was stirred, a solution obtained by dissolving 14.8 g (74.8 mmol) of trimethyltin chloride in 100 ml of degassed and dried tetrahydrofuran was added dropwise thereto. After further stirring at room temperature for 4 hours, the solvent was distilled off under reduced pressure. Next, 150 ml of degassed and dried hexane was added to the solution to carry out extraction, and the solvent was distilled off under reduced pressure to obtain 15.07 g (27.2 mmol, yield: 73%) of (1,1'-dimethylsilylene)(2,2'-isopropylidene)-4,4'-bis(trimethyltin)-bis(cyclopentadiene) (Compound f):

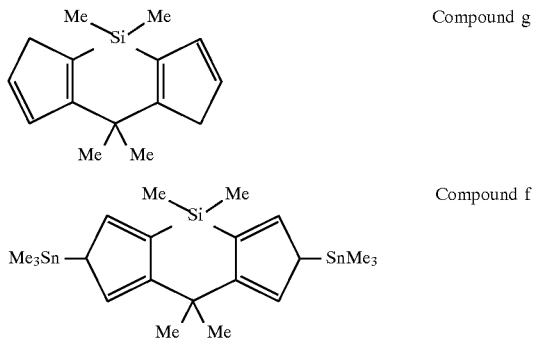

(2) Preparation of (1,1'-dimethylsilylene)(2,2'-isopropylidene)-bis(cyclopentadienyl)titanium dichloride (A-6)

In a 300-ml three-necked flask equipped with a reflux condenser and purged with nitrogen was placed 6.15 g (11.1 mmol) of (1,1'-dimethylsilylene)(2,2'-isopropylidene)-4,4'-bis(trimethyltin)-bis(cyclopentadiene) obtained in the above-mentioned (1), and 100 ml of degassed and dried toluene was then added thereto. While this solution was stirred, 1.22 ml (11.1 mmol) of titanium tetrachloride diluted with 50 ml of degassed and dried toluene was added dropwise thereto under a nitrogen gas stream, and the solution was then heated under reflux for 4 hours on an oil bath. Next, the solvent was distilled off under reduced pressure, and the resultant residue was washed with 100 ml of degassed and dried hexane and then 100 ml of degassed and dried diethyl ether. Afterward, the solution was dried under reduced pressure, and then extracted with 200 ml of degassed and dried toluene. The extract was concentrated under reduced pressure, and then cooled to −20° C. to obtain 1.81 g (5.24 mmol, yield: 47.2%) (1,1'-dimethylsilylene)-(2,2'-isopropylidene)-bis(cyclopentadienyl)titanium dichloride in the state of a dark red crystal.

(3) Preparation of catalyst

Mixed were 2.0 g of silica (trade name Debison 952, made by Fuji Debison Co., Ltd.) which had been calcined at 400° C. for 48 hours, 100 ml of toluene and 30 mmol of methylaluminoxane, and the mixture was then reacted at 40° C. for 2 hours. The resultant solid was collected by filtration, and then sufficiently washed with toluene. Next, 100 ml of toluene and 0.1 mmol of a titanium complex (A-6) obtained in the above-mentioned (2) were added to the washed solid, and reaction was carried out at 40° C. for 2 hours. The obtained solid was collected by filtration, sufficiently washed with toluene, and then dried under reduced pressure to prepare a carried catalyst.

In this catalyst, there were contained 5.82 wt % of an aluminum atom and 0.07 wt % of a titanium atom.

(4) Polymerization

In a 1-liter autoclave heated and dried under reduced pressure were placed 390 ml of hexane and 10 ml of 1-octene at room temperature in a nitrogen atmosphere, and a carried catalyst (Al=7.0×10$^{-4}$ mol, Ti=5.0×10$^{-4}$ mol) obtained in the above-mentioned (3) was fed thereto, followed by heating the mixture up to 80° C. Afterward, while ethylene was continuously fed thereto at 80° C. so as to maintain 8 atm, polymerization was carried out for 30 minutes to obtain 2.4 g of a polymer.

EXAMPLE 27

Preparation of (1,1'-dimethylsilylene)(2,2'-isopropylidene)-(3-methylindenyl)(3'-methylindenyl)-zirconium dichloride (A-7)

(1) In a Schlenk tube purged with nitrogen were placed 6.0 g (18.3 mmol) of the Compound d obtained in Example 16 and 150 ml of diethyl ether. Next, the solution was cooled to 0° C., and 43.5 ml (73.2 mmol) of an n-butyl-lithium solution having a concentration of 1.6 mol/liter was added dropwise thereto. The temperature of the solution was returned to room temperature, and at this time, a pink precipitate was gradually deposited. After stirring at room temperature for 12 hours, the solvent was distilled off, and the precipitate was then washed twice with hexane. Next, the precipitate was dried under reduced pressure to obtain a dilithium salt (hereinafter referred to as "Compound e") in the state of a pink powder.

(2) A dilithium salt (Compound e) obtained above was dissolved in 150 ml of THF, and 10.4 g (73.2 mmol) of methyl iodide was slowly added dropwise at room temperature. Next, the solution was heated up to 50° C., and then stirred for 5 hours. Afterward, the solvent was distilled off, and extraction was done with dichloromethane and water. The resultant organic layer was washed twice with water, dehydrated over magnesium sulfate, and then filtered. The solvent was distilled off, thereby obtaining 6.2 g (17.4 mmol) of a desired product (the following Compound h) in the state of an oil:

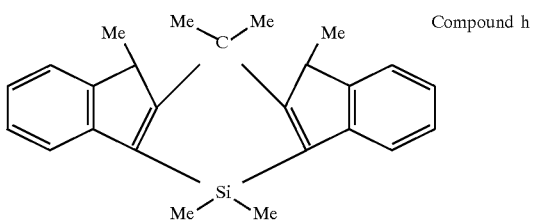

(3) In a Schlenk tube purged with nitrogen were placed 6.2 g (17.4 mmol) of a Compound h and 150 ml of diethyl ether. Next, the solution was cooled to 0° C., and 43.5 ml (69.0 mmol) of an n-butyllithium solution having a concentration of 1.6 mol/liter was added dropwise thereto. The temperature of the solution was returned to room temperature, and at this time, a white precipitate was gradually deposited. After stirring at room temperature for 12 hours, the solvent was distilled off, and the precipitate was washed twice with hexane. Next, the precipitate was dried under reduced pressure to obtain a dilithium salt (the following Compound i):

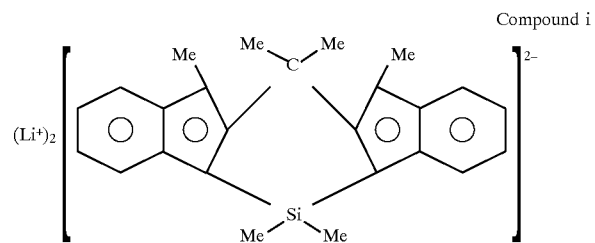

(4) 100 ml of toluene was added to the dilithium salt (Compound i) obtained above to form a suspension. In another Schlenk tube, tetrachlorozirconium (800 mg, 3.4 mmol) was mixed with 100 ml of toluene to form another suspension, and this suspension was cooled to −78° C. Afterward, the above-mentioned suspension containing the dilithium salt was slowly added dropwise to the cooled suspension. The temperature of the mixed suspension was returned to room temperature, and it was then heated up to 80° C., followed by stirring for 6 hours. A precipitate was removed by filtration, and the solvent was then distilled off.

After the resultant residue was washed with hexane, recrystallization was carried out from diethyl ether to obtain 1.0 g of a yellow crystal which was the following (A-7).

The $^1$H-NMR of this product was measured, and the following results were obtained.

$^1$H-NMR (CDCl$_3$): δ 0.89 (s, 3H, SiCH$_3$), 1.15 (s, 3H, SiCH$_3$), 1.92 (s, 3H, CCH$_3$), 2.36 (s, 3H, CCH$_3$), 2.47 (s, 6H, CpCH$_3$), 6.9–7.6 (mul, 8H, Ind-H)

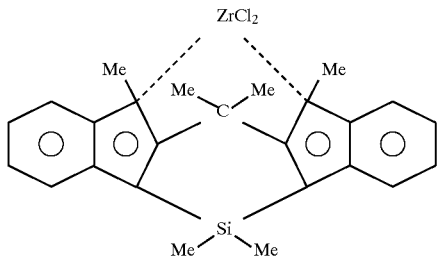

(5) Polymerization (i)
Preparation of ethylene-1-octene copolymer

In a 1-liter autoclave heated and dried under reduced pressure were placed 360 ml of toluene, 40 ml of 1-octene and 5 ml of methylaluminoxane (MAO) at room temperature in a nitrogen atmosphere, and the temperature of the solution was then raised up to 60° C. with stirring. Afterward, 1 μmol of the above-mentioned (A-7) was added thereto, and the solution was then heated up to 80° C. Next, while ethylene was continuously introduced thereinto at 80° C. so as to maintain 8 atm, polymerization was carried out for 20 minutes. After the completion of the reaction, the reaction solution was poured into a methanol-hydrochloric acid solution, and the resultant polymer was washed three times with methanol, followed by drying under reduced pressure. The yield of the polymer was 54.4 g, and its melting point (Tm) was 108° C. and its intrinsic viscosity [η] was 1.59 dl/g.

(6) Polymerization (ii)

The same procedure as in the above-mentioned (5) was repeated except that 5 mmol of methylaluminoxane was replaced with 6 mmol of tetraisobutyldialuminoxane. Yield was 3.1 g.

(7) Polymerization (iii)

The same procedure as in the above-mentioned (6) was repeated except that 6 mmol of tetraisobutyldialuminoxane was replaced with 1 μmol of trisiobutylaluminum and 2 μmol of tris(pentafluorophenyl)borane. Yield was 2.5 g.

EXAMPLE 28

(1) Synthesis of ethyl(2-indenyl) acetate (Compound j)

Under a nitrogen gas stream, 3.3 g (0.14 mol) of sodium hydride was suspended in 300 ml of THF, and the suspension was then cooled to 10° C. To the cooled suspension, a THF solution (200 ml of THF) containing 28.3 g (0.11 mol) of ethyldiethyl phosphonoacetate was added dropwise over 1 hour. After the dropping, the suspension was stirred at room temperature for 30 minutes, and then ice-cooled. Next, a THF solution (75 ml of THF) containing 16.3 g (0.12 mol) of 2-indanone was added dropwise over 1 hour. After the dropping, the solution was stirred at room temperature for 30 minutes, and hydrolysis was carried out with water. Extraction was done with 500 ml of diethyl ether, and the resultant organic layer was then separated. This organic layer was dried over anhydrous magnesium sulfate, and the solvent was then distilled off under reduced pressure. The resultant residue was subjected to vacuum distillation (3 mmHg, 107°–117° C.), thereby obtaining a desired product (Compound k) in the state of a light yellow oil.

The $^1$H-NMR of this product was measured, and the following results were obtained.

$^1$H-NMR (CDCl$_3$): 1.23 (t, 3H), 3.40 (s, 2H), 3.45 (s, 2H), 4.16 (q, 2H), 6.65 (s, 1H)

(2) Synthesis of 2-(2-indenyl)-ethanol (Compound l)

Under a nitrogen gas stream, 2.2 g (58.49 mmol) of lithiumaluminum hydride was suspended in 100 ml of diethyl ether. To this suspension, a diethyl ether solution (50 ml of diethyl ether) containing 11 g (59.06 mmol) of the above-mentioned compound k was added dropwise over 1 hour. After the dropping, the solution was stirred at room temperature for 30 minutes. After ice-cooling, 50 ml of water was slowly added, and dilute hydrochloric acid was further added thereto so as to dissolve impurities. The resultant oil layer was separated, and the solvent was distilled off under reduced pressure to obtain a desired compound (Compound l) in the state of a white solid. Its yield was 7.89 g.

The $^1$H-NMR of this product was measured, and the following results were obtained.

$^1$H-NMR (CDCl$_3$): 1.56 (S, 1H), 2.76 (t, 2H), 3.37 (s, 2H), 3.83 (t, 2H)

(3) Synthesis of 1-bromo-2-indenylethane (Compound m)

Under a nitrogen gas stream, 4.61 g (28.77 mmol) of the above-mentioned Compound l was dissolved in 65 ml of dichloromethane. To this solution, 7.66 g (29.20 mmol) of trimethylphosphine was added. Next, 5.19 g (29.16 mmol) of N-bromosuccinimide was slowly added. After the addition of N-bromosuccinimide, the solution was stirred at room temperature for 30 minutes. Water was added to the reaction mixture, and the mixture was further stirred. The resultant organic layer was separated and then dried over magnesium sulfate, and the solvent was distilled off under reduced pressure. The residue was purified through a silica gel column (developing solvent: hexane) to obtain a desired product (Compound m) in the state of a colorless oil. Its yield was 5.07 g, i.e., 80.85%.

The $^1$H-NMR of this product was measured, and the following results were obtained.

$^1$H-NMR (CDCl$_3$): 3.20 (t, 2H), 3.32 (s, 2H), 3.52 (t, 2H), 6.60 (s, 1H), 6.93–7.53 (m, 4H)

(4) Synthesis of (2,2'-ethylene)-(cyclopentadiene)-(indene) (Compound n)

Under a nitrogen gas stream, 18 mmol of a sodium salt of cyclopentadiene was dissolved in 100 ml of THF, and the solution was then cooled to –30° C. To this solution, a THF solution (30 ml of THF) containing 2 g (8.96 mmol) of the above-mentioned Compound m was added dropwise over 1 hour. Next, the reaction mixture was stirred at room temperature for 16 hours, and then hydrolyzed. Extraction was carried out with dichloromethane, and the resultant oil layer was separated and then dried over anhydrous sodium sulfate. Afterward, the solvent was distilled off under reduced pressure, and the residue was purified through a silica gel column (developing solvent: hexane) to obtain a desired product (Compound n) in the state of a white solid. Its yield was 1.66 g, i.e., 59.4%.

The $^1$H-NMR of this product was measured, and the following results were obtained.

$^1$H-NMR: 2.73 (S, 4H), 2.91 (m, 2H), 3.30 (S, 2H), 5.95–6.65 (m, 4H), 6.86–7.53 (m, 4H)

(5) Synthesis of (1,1'-dimethylsilylene)(2,2'-ethylene)-(cyclopentadiene)(indene) (Compound o)

1.66 g (7.96 mmol) of the above-mentioned Compound n was dissolved in 100 ml of hexane, and the solution was then cooled to –78° C. To this solution, 9.8 ml (15.97 mmol) of a hexane solution containing 1.63 mmol of n-butyllithium per ml of hexane was added dropwise over 30 minutes. After the completion of the dropping, the solution was stirred at room temperature for 12 hours. The resultant white precipitate was collected by filtration and then washed with hexane, and the solvent was distilled off under reduced pressure. In consequence, 1.51 g (6.85 mmol) of a white powder (a dilithium salt of Compound n) was obtained. The thus obtained dilithium salt was dissolved in 100 ml of THF, and the solution was then cooled to −78° C. To this solution, a THF solution (50 ml of THF) containing 0.83 ml (6.83 mmol) of dichlorodimethylsilane was added dropwise over 1 hour. After the completion of the dropping, the solution was stirred at room temperature for 6 hours, and THF was distilled off under reduced pressure and extraction was then carried out with dichloromethane. Afterward, dichloromethane was distilled off under reduced pressure to obtain a Compound o. Its yield was 1.80 g. The $^1$H-NMR of this product was measured, and the following results were obtained.

$^1$H-NMR (CDCl$_3$): 0.22 (s, 3H), 0.55 (s, 3H), 2.78 (s, 4H), 3.82–3.92 (2H), 6.04–6.80 (m, 4H), 6.88–7.70 (m, 4H)

(6) Preparation of (1,1'-dimethylsilylene)(2,2'-ethylene)-(cyclopentadienyl)(indenyl)zirconium dichloride (A-8)

100 ml of hexane was added to 1.80 g of the above-mentioned Compound o, and the solution was cooled to −78° C. To the cooled solution, 8.4 ml (13.7 mmol) of a hexane solution containing 1.63 mol of n-butyllithium per liter of hexane was added dropwise over 1 hour. After the completion of the dropping, the temperature of the solution was raised to room temperature, followed by stirring for 12 hours. The resultant white precipitate was collected by filtration, and then washed with hexane to obtain 1.80 g (6.51 mmol) of a dilithium salt of the Compound o. To this dilithium salt, 100 ml of toluene was added, and the suspension was then cooled to −78° C. Next, a toluene suspension (50 ml of toluene) containing 1.5 g (6.44 mmol) of zirconium tetrachloride was added to the cooled suspension over about 30 minutes. Afterward, the temperature of the reaction mixture was raised to room temperature, and the mixture was stirred for 12 hours as it was. Next, the supernatant liquid was collected by filtration, and then evaporated to dryness under reduced pressure. The resultant residue was recrystallized from dichloromethane and hexane, and extraction with heptane was then carried out. As a result of this serial operation, a desired compound (A-8) was obtained in the state of a light yellow solid. Its yield was 73 mg, i.e., 2.5%.

The $^1$H-NMR of this product was measured, and the following results were obtained.

$^1$H-NMR (CDCl$_3$): 0.11 (s, 3H), 0.19 (s, 3H), 3.15 (4H), 6.0–7.7 (m, 8H)

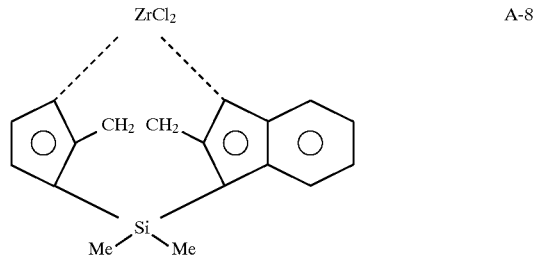

A-8

(7) Polymerization of ethylene

In a heated and dried 1-liter autoclave were placed 400 ml of toluene and 2.39 mmol of methylaluminoxane at room temperature under a nitrogen gas stream. After the temperature of this mixture was raised up to 60° C., 2.27 μmol of the above-mentioned (A-8) was added thereto, and this mixture was further heated up to 80° C. When 80° C. had been reached, the pressure of ethylene was raised up to 8 kg/cm$^2$. In this state, polymerization was carried out for 30 minutes. After the completion of the reaction, the reaction product was poured into methanol, and the resultant polymer was collected by filtration, washed with methanol, and then heated/dried under reduced pressure, thereby obtaining 78.6 g of a polyethylene. Its intrinsic viscosity [η] was 3.07 dl/g.

Possibility of Industrial Utilization

A transition metal compound of the present invention is a novel multiple crosslinking type compound, and it is useful as a catalytic component for olefin polymerization. Furthermore, according to a method of the present invention, this transition metal compound and a compound usable as a precursor of its ligand can efficiently be prepared. In addition, a catalyst for the olefin polymerization of the present invention has a high activity and an excellent copolymerizability, and so when this catalyst is used, an olefin polymer having a uniform composition and a narrow molecular weight distribution can efficiently be obtained.

We claim:

1. A catalyst for olefin polymerization which comprises a transition metal compound represented by the general formula (I) below and an activation cocatalyst, wherein the general formula (I) is

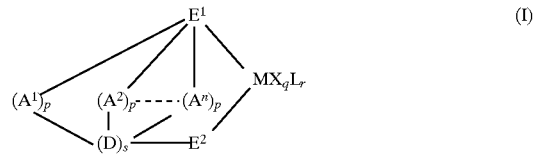

(I)

wherein M is Ti, Zr or Hf, E$^1$ and E$^2$ are each a cyclopentadienyl group, a substituted cyclopentadienyl group, an indenyl group or substituted indenyl group, and they form a crosslinking structure via (A$^1$)$_p$, (A$^2$)$_p$, ... (A$^n$)$_p$ and (D)$_s$, and they may be the same or different; X is a σ-bonding ligand, and when a plurality of Xs are present, these plural Xs may be the same or different and each X may cross-link with E$^1$, E$^2$ or L; L is a Lewis base, and when a plurality of Ls are present, these plural Ls may be the same or different, and each L may cross-link with E$^1$, E$^2$ or X; A$^1$, A$^2$, ... A$^n$ are each a crosslinking group consisting of at least one element which is C, H, Si, O, N, S, or P and they may be the same or different, but at least one of them comprises a crosslink consisting of carbon alone; D is a crosslinking group consisting of at least one element which is C, H, Si, O, N or P, and when a plurality of Ds are present, these plural Ds may be the same or different; n is an integer of 2 to 4; p is an integer of 1 to 4, and the respective ps may be the same or different; q is an integer of 1 to 5 and is (the valence of M)−2; r is an integer of 0 to 3; and s is an integer of 0 to 4, and when s is 0, (A$^1$)$_p$, (A$^2$)$_p$, ... (A$^n$)$_p$ and E$^2$ form a direct bond.

2. The catalyst for olefin polymerization according to claim 12 wherein at least one of A$^1$, A$^2$, ... A$^n$ is a crosslinking group consisting of

wherein R is a hydrogen atom, a halogen atom, a hydrocarbon group having 1 to 20 carbon atoms or halogen-containing hydrocarbon group having 1 to 20 carbon atoms.

3. The catalyst for olet-in polymerization according to claim 1, wherein E$^1$ and E$^2$ are each a cyclopentadienyl group or a substituted cyclopentadienyl group.

4. The catalyst for olefin polymerization according to claim 2 wherein E¹ and E² are each a cyclopentadienyl group or a substituted cyclopentadienyl group.

5. The catalyst for olefin polymerization according to claim 2 wherein at least one of E¹ and E² is an indenyl group or a substituted indenyl group.

6. A catalyst for olefin polymerization which comprises a transition metal compound represented by the general formula (II) and an activation cocatalyst, where the general formula (II) is

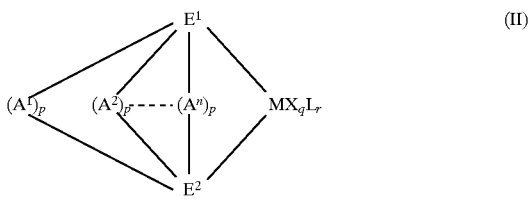

wherein M is Ti, Zr or Hf, E¹ and E² are each a cyclopentadienyl group, a substituted cyclopentadienyl group, an indenyl group or a substituted indenyl group, and they form a cross-linking structure via $(A^1)_p$, $(A^2)$, ... $(A^n)_p$, and they may be the same or different; X is a σ-bonding ligand, and when a plurality of Xs are present, these plural Xs may be the same or different and each X may cross-link with E¹, E² or L; L is a Lewis base, and when a plurality of Ls are present, these plural Ls may be the same or different, and each L may cross-link with E¹, E² or X; $A^1, A^2, \ldots A^n$ are each a crosslinking group consisting of at least one element which is C, H, Si, O, N, S or P and they may be the same or different, but at least one of them comprises a crosslink consisting of carbon alone; n is an integer of 2 to 4; p is an integer of 1 to 4, and the respective ps may be the same or different; q is an integer of 1 to 5 and is (the valence of M)–2; r is an integer of 0 to 3.

7. The catalyst for olefin polymerization according to 6 wherein at least one of $Al^1, A^2, \ldots A^n$ is a crosslinking group consisting of

wherein R is a hydrogen atom, a halogen atom, a hydrocarbon group having 1 to 20 carbon atoms or a halogen-containing hydrocarbon group having 1 to 20 carbon atoms.

8. The catalyst for olefin polymerization according to claim 6, wherein E¹ and E² are each a cyclopentadienyl group or a substituted cyclopentadienyl group.

9. The catalyst for olefin polymerization according to claim 7 wherein E¹ and E² are each a cyclopentadienyl group or a substituted cyclopentadienyl group.

10. The catalyst for olefin polymerization according to claim 7 wherein at least one of E¹ and E² is an indenyl group or a substituted indenyl group.

11. A catalyst for olefin polymerization which comprises (A) a transition metal compound according to the general formula (I) below and (B) a compound capable of reacting with the component (A) to form an ionic complex, where the general formula (I) is

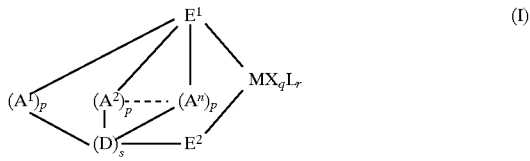

wherein M is ri, Zr or Hf. E¹ and E² are each a cyclopentadienyl group, a substituted cyclopentadienyl group, an indenyl group or substituted indenyl group, and they form a cross-linking structure via $(A^1)_p$, $(A^2)_p$, ... $(A^1)_p$ and $(D)_s$, and they may be the same or different; X is a σ-bonding ligand, and when a plurality of Xs are present, these plural Xs may be the same or different and each X may cross-link with E¹, E² or L; L is a Lewis base, and when a plurality of Ls are present, these plural Ls may be the same or different, and each L may cross-link with E¹, E² or X; $A^1, A^2, \ldots A^n$ are each a crosslinking group consisting of at least one element which is C, H, Si, O, N, S or P and they may be the same or different, but at least one of them comprises a crosslink consisting of carbon alone; D is a crosslinking group consisting of at least one element which is C, H, Si, O, N or P, and when a plurality of Ds are present, these plural Ds may be the same or different; n is an integer of 2 to 4; p is an integer of 1 to 4, and the respective ps may be the same or different; q is an integer of 1 to 5 and is (the valence of M)–2; r is an integer of 0 to 3; and s is an integer of 0 to 4, and when s is 0, $(A^1)_p$, $(A^2)_p$, ... $(A^n)_p$ and E² form a direct bond.

12. The catalyst for olefin polymerization according to 11 wherein at least one of $A^1, A^2, \ldots A^n$ is a crosslinking group consisting of

wherein R is a hydrogen atom, a halogen atom, a hydrocarbon group having 1 to 20 carbon atoms or a halogen-containing hydrocarbon group having 1 to 20 carbon atoms.

13. The catalyst for olefin polymerization according to claim 11, wherein E¹ and E2 are each a cyclopentadienyl group or a substituted cyclopentadienyl group.

14. The catalyst for olefin polymerization according to claim 12 wherein E¹ and E² are each a cyclopentadienyl group or a substituted cyclopentadienyl group.

15. The catalyst for olefin polymerization according to claim 12 wherein at least one of E¹ and E² is an indenyl group or a substituted indenyl group.

16. A catalyst for olefin polymerization which comprises (A) a transition metal compound according to the general formula (II) below and (B) a compound capable of reacting with the transition metal compound of the component (A) to form an ionic complex, where the general formula (II) is

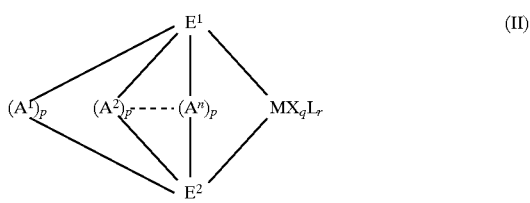

wherein M is Ti, Zr or Hf, E¹ and E² are each a cyclopentadienyl group, a substituted cyclopentadienyl group, an indenyl group or a substituted indenyl group, and they form a cross-linking structure via $(A^1)_p$, $(A^2)$, ... $(A^n)_p$, and they may be the same or different; X is a σ-bonding ligand, and when a plurality of Xs are present, these plural Xs may be the same or different and each X may cross-link with $E^1$, $E^2$ or L; L is a Lewis base, and when a plurality of Ls are present, these plural Ls may be the same or different, and each L may cross-link with $E^1$, $E^2$ or X; $A^1$, $A^2$, ... $A^n$ are each a crosslinking group consisting of at least on element which is C, H, Si, O, N, S or P and they may be the same or different, but at least one of them comprises a crosslink consisting of carbon alone; n is an integer of 2 to 4; p is an integer of 1 to 4, and the respective ps may be the same or different; q is an integer of 1 to 5 and is (the valence of M)−2; and r is an integer of 0 to 3.

17. The catalyst for olefin polymerization according to 16 wherein at least one of $A^1$, $A^2$, ... $A^n$ is a crosslinking group consisting of

wherein R is a hydrogen atom, a halogen atom, a hydrocarbon group having 1 to 20 carbon atoms or a halogen-containing hydrocarbon group having 1 to 20 carbon atoms.

18. The catalyst for olefin polymerization according to claim 16, wherein $E^1$ and $E^2$ are each a cyclopentadienyl group or a substituted cyclopentadienyl group.

19. The catalyst for olefin polymerization according to claim 17 wherein $E^1$ and $E^2$ are each a cyclopentadienyl group or a substituted cyclopentadienyl group.

20. The catalyst for olefin polymerization according to claim 17 wherein at least one of $E^1$ and $E^2$ is an indenyl group or a substituted indenyl group.

21. A catalyst for olefin polymerization which comprises (A) a transition metal compound according to the general formula (I) below, (B) a compound capable of reacting with the component (A) to form an ionic complex, and (C) an organic aluminum compound, where the general formula (I) is

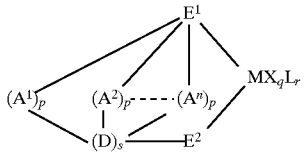

wherein M is Ti, Zr or Hf, $E^1$ and $E^2$ are each a cyclopentadienyl group, a substituted cyclopentadienyl group, an indenyl group or substituted indenyl group, and they form a cross-linking structure via $(A^1)_p$, $(A^2)_p$, ... $(A^n)_p$ and $(D)_s$, and they may be the same or different; X is a σ-bonding ligand, and when a plurality of Xs are present, these plural Xs may be the same or different and each X may cross-link with $E^1$, $E^2$ or L; L is a Lewis base, and when a plurality of Ls are present, these plural Ls may be the same or different, and each L may cross-link with $E^1$, $E^2$ or X; $A^1$, $A^2$, ... $A^n$ are each a crosslinking group consisting of at least one element which is C, H, Si, O, N, S or P and they may be the same or different, but at least one of them comprises a crosslink consisting of carbon alone; D is a crosslinking group consisting of at least one element which is C, H, Si, O, N or P, and when a plurality of Ds are present, these plural Ds may be the same or different; n is an integer of 2 to 4; p is an integer of 1 to 4, and the respective ps may be the same or different; q is an integer of 1 to 5 and is (the valence of M)−2; r is an integer of 0 to 3; and s is an integer of 0 to 4, and when s is 0, $(A^1)_p$, $(A^2)_p$, ... $(A^n)_p$ and $E^2$ form a direct bond.

22. The catalyst for olefin polymerization according to 21 wherein at least one of $A^1$, $A^2$, ... $A^n$ is a crosslinking group consisting of

wherein R is a hydrogen atom, a halogen atom, a hydrocarbon group having 1 to 20 carbon atoms or a halogen-containing hydrocarbon group having 1 to 20 carbon atoms.

23. The catalyst for olefin polymerization according to claim 21, wherein $E^1$ and $E^2$ are each a cyclopentadienyl group or a substituted cyclopentadienyl group.

24. The catalyst for olefin polymerization according to claim 22 wherein $E^1$ and $E^2$ are each a cyclopentadienyl group or a substituted cyclopentadienyl group.

25. The catalyst for olefin polymerization according to claim 22 wherein at least one of $E^1$ and $E^2$ is an indenyl group or a substituted indenyl group.

26. A catalyst for olefin polymerization which comprises (A) a transition metal compound according to the general formula (II) below, (B) a compound capable of reacting with the transition metal compound of the component (A) to form an ionic complex, and (C) an organic aluminum compound, where the general formula (II) is

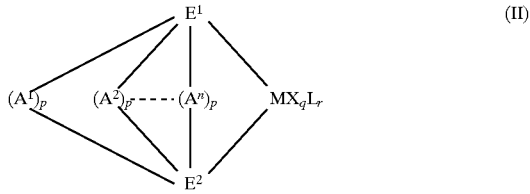

wherein M is Ti, Zr or Hf, $E^1$ and $E^2$ are each a cyclopentadienyl group, a substituted cyclopentadienyl group, an indenyl group or a substituted indenyl group, and they form a cross-linking structure via $(A^1)_p$, $(A^2)$, ... $(A^n)_p$, and they may be the same or different; X is a σ-bonding ligand, and when a plurality of Xs are present, these plural Xs may be the same or different and each X may cross-link with $E^1$, $E^2$ or L; L is a Lewis base, and when a plurality of Ls are present, these plural Ls may be the same or different, and each L may cross-link with $E^1$, $E^2$ or X; $A^1$, $A^2$, ... $A^n$ are each a crosslinking group consisting of at least one element which is C, H, Si, O, N, S or P and they may be the same or different, but at least one of them comprises a crosslink consisting of carbon alone; n is an integer of 2 to 4; p is an integer of 1 to 4, and the respective ps may be the same or different; q is an integer of 1 to 5 and is (the valence of M)−2; and r is an integer of 0 to 3.

27. The catalyst for olefin polymerization according to 26 wherein at least one of $A^1$, $A^2$, ... $A^n$ is a crosslinking group consisting of

wherein R is a hydrogen atom, a halogen atom, a hydrocarbon group having 1 to 20 carbon atoms or a halogen-containing hydrocarbon group having 1 to 20 carbon atoms.

28. The catalyst for olefin polymerization according to claim 26, wherein $E^1$ and $E^2$ are each a cyclopentadienyl group or a substituted cyclopentadienyl group.

29. The catalyst for olefin polymerization according to claim 27 wherein $E^1$ and $E^2$ are each a cyclopentadienyl group or a substituted cyclopentadienyl group.

30. The catalyst for olefin polymerization according to claim 27 wherein at least one of $E^1$ and $E^2$ is an indenyl group or a substituted indenyl group.

31. A process for preparing an olefin polymer which comprises the step of homopolymerizing a olefin, or copolymerizing an olefin, another olefin and/or another monomer other than the olefin in the presence of a catalyst for olefin polymerization as claimed in claim 1.

32. A process for preparing an olefin polymer which comprises the step of homopolymerizing an olefin, or copolymerizing an olefin, another olefin and/or another monomer other than the olefin in the presence of a catalyst for olefin polymerization as claimed in claim 2.

33. A process for preparing an olefin polymer which comprises the step of homopolymerizing a olefin, or copolymerizing an olefin, another olefin and/or another monomer other than the olefin in the presence of a catalyst for olefin polymerization as claimed in claim 6.

34. A process for preparing an olefin polymer which comprises the step of homopolymerizing an olefin, or copolymerizing an olefin, another olefin and/or another monomer other than the olefin in the presence of a catalyst for olefin polymerization as claimed in claim 7.

35. A process for preparing an olefin polymer which comprises the step of homopolymerizing a olefin, or copolymerizing an olefin, another olefin and/or another monomer other than the olefin in the presence of a catalyst for olefin polymerization as claimed in claim 11.

36. A process for preparing an olefin polymer which comprises the step of homopolymerizing an olefin, or copolymerizing an olefin, another olefin and/or another monomer other than the olefin in the presence of a catalyst for olefin polymerization as claimed in claim 12.

37. A process for preparing an olefin polymer which comprises the step of homopolymerizing a olefin, or copolymerizing an olefin, another olefin and/or another monomer other than the olefin in the presence of a catalyst for olefin polymerization as claimed in claim 16.

38. A process for preparing an olefin polymer which comprises the step of homopolymerizing an olefin, or copolymerizing an olefin, another olefin and/or another monomer other than the olefin in the presence of a catalyst for olefin polymerization as claimed in claim 17.

39. A process according to claim 38, wherein the olefin is ethylene or propylene or a mixture of ethylene with I-octene and wherein the transition, metal compound (A) is (1,1'-dimethylsilylene)(2,2'-isopropylidene)-bis(cyclopentadienyl) zirconium dichloride or (1,1'-dimethylsilylene)(2,2'-isopropylidene)-bis(cyclopentadienyl)titanium dichloride.

40. A process according to claim 38 wherein the olefin is ethylene or propylene or a mixture of ethylene with I-octene and wherein the transition metal compound (A) is (1,1'-dimethylsilylene)(2,2'-isopropylidene)-(3-methylindenyl)(3'-methylindenyl)-zirconium dichloride or (1,1'-dimethylsilylene)(2,2'-ethylene)-(cylopentadienyl)(indenyl) zirconium dichloride.

41. A process for preparing an olefin polymer which comprises the step of homopolymerizing a olefin, or copolymerizing an olefin, another olefin and/or another monomer other than the olefin in the presence of a catalyst for olefin polymerization as claimed in claim 21.

42. A process for preparing an olefin polymer which comprises the step of homopolymerizing an olefin or copolymerizing an olefin, another olefin and/or another monomer other than the olefin in the presence of a catalyst for olefin polymerization as claimed in claim 22.

43. A process for preparing an olefin polymer which comprises the step of homopolymerizing a olefin, or copolymerizing an olefin, another olefin and/or another monomer other than the olefin in the presence of a catalyst for olefin polymerization as claimed in claim 26.

44. A process for preparing an olefin polymer which comprises the step of homopolymerizing an olefin, or copolymerizing an olefin, another olefin and/or another monomer other than the olefin in the presence of a catalyst for olefin polymerization as claimed in claim 27.

* * * * *